United States Patent [19]
Schiestl et al.

[11] Patent Number: 5,792,633
[45] Date of Patent: Aug. 11, 1998

[54] PROCESS FOR GENE TARGETING AND GENOME MANIPULATIONS

[75] Inventors: Robert H. Schiestl, Boston, Mass.; Thomas D. Petes, Chapel Hill, N.C.; Stephanie E. Kong, Boston, Mass.

[73] Assignee: GeneBioMed, Inc., East Rochester, N.Y.

[21] Appl. No.: 338,471

[22] PCT Filed: May 21, 1993

[86] PCT No.: PCT/US93/04847

§ 371 Date: Dec. 12, 1994

§ 102(e) Date: Dec. 12, 1994

[87] PCT Pub. No.: WO93/23534

PCT Pub. Date: Nov. 25, 1993

Related U.S. Application Data

[63] Continuation-in-part of Ser. No. 944,665, Sep. 14, 1992, abandoned, which is a continuation-in-part of Ser. No. 887,689, May 21, 1992, abandoned.

[51] Int. Cl.$^6$ .......................... C12N 15/09; C12N 15/63; C12N 15/87
[52] U.S. Cl. ...................................... 435/172.3; 435/172.1
[58] Field of Search .............................. 435/172.3, 172.1

[56] References Cited

PUBLICATIONS

Gusew et al., "Linear DNA must have free ends to transform rat cells efficiently". Mol. Gen. Genet. 206: 121–125. 1987.

Kuspa et al., "Tagging developmental genes in Dictyostelium by restriction enzyme–mediated integration of plasmid DNA", Proc. Natl. Acad. Sci. USA 89: 8803–8807. Sep. 15, 1992.

Schiestl et al. "Integration of DNA fragments by illegitimate recombination in Saccharomyces cerevisiae", Proc. Natl. Acad. Sci. USA 88: 7585–7589. Sep. 1, 1991.

Marx, "Dictyostelium researchers expect gene bonanza", Science 258: 402–403. Oct. 16, 1992.

Grimm et al. "Observations on integrative transformation in Schizosaccharomyces pombe". Mol. Gen. Genet. 215: 87–93. 1988.

Chang et al. "In vivo site–specific genetic recombination promoted by the EcoRI restriction endonuclease" Proc. Natl. Acad. Sci. USA 74: 4811–4815. Nov. 1977.

*Primary Examiner*—Jasemine C. Chambers
*Assistant Examiner*—Scott D. Priebe
*Attorney, Agent, or Firm*—Howard J. Greenwald

[57] ABSTRACT

A process for insertional mutagenesis and genome manipulations of yeast cells. In the first step of this process, viable yeast cells are combined with a restriction enzyme cleaved deoxyribonucleic acid fragment which lacks substantial sequence identity and shows no specific hybridization signals with the DNA of the viable yeast cells. The viable yeast cells are then transformed so that the cleaved deoxyribonucleic acid fragment is incorporated into the yeast cells by nonhomologous recombination; and the transformed yeast cells are then incubated in the presence of a growth medium.

3 Claims, 5 Drawing Sheets

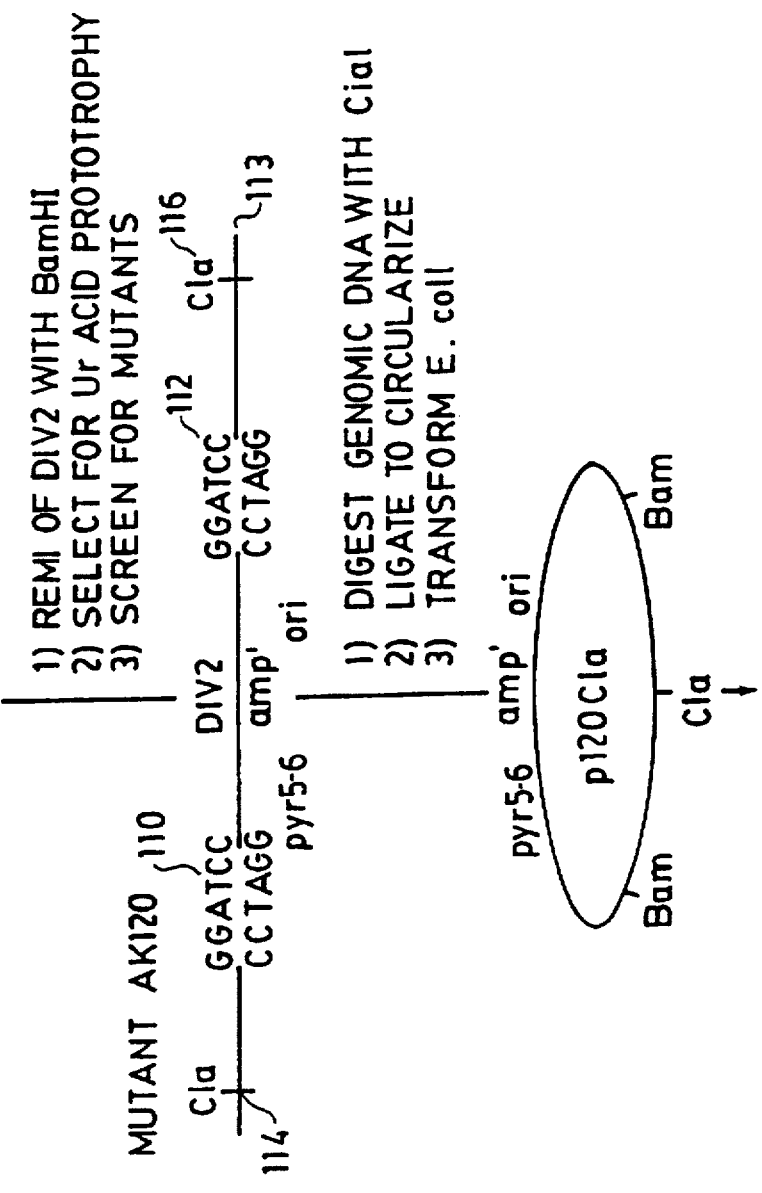

PROCESS FOR GENE TARGETING AND GENOME MANIPULATIONS

DESCRIPTION

This application is a 371 of PCT/US93/04847 filed May 21, 1993, which is a continuation-in-part of U.S. application Ser. No. 07/944,665 filed Sep. 14, 1992, now abandoned, which is a continuation-in-part of U.S. application Ser. No. 07/887,689 filed May 21, 1992, now abandoned.

TECHNICAL FIELD

A process to detect illegitimate recombination and restriction enzyme mediated recombination in the yeast *Saccharomyces cerevisiae*, in the slime mold *Dictyostelium discoideum* and in mammalian cells.

BACKGROUND ART

More than 3,000 diseases are caused by mutations such as, for example, hemophilia, Tay-Sachs disease, Duchenne's muscular dystrophy, Huntington's disease, alpha-thalassemia, Lesch Nyhan syndrome, etc. Most of these diseases cannot be treated medically.

The science of gene therapy is in its infancy. Gene therapy aims to cause a reversion of the genetic basis of a disease and, thus after one successful treatment, to cure the patient for life; see, e.g., pages 411–441 of a book edited by R. Kucherlapati entitled "Gene Transfer" (Plenum Press, New York, 1986).

Gene therapy attempts to determine the existence and location of a mutated gene and, thereafter, to add a wild type copy of the mutated gene to the cells to thereby replace the mutated gene with the wild type copy; this procedure is often referred to as "gene targeting."

In mammalian cells, however, it is known that genes introduced into such cells integrate into the DNA of the cell primarily at nonhomologous sites; thus, instead of replacing a mutated gene, the wild type copy will be introduced at another locus in the DNA. The DNA so integrated will be more likely to cause mutations than it would have been prior to such integration, for it is known that random integration of genes into mammalian cells is mutagenic. See, e.g., W. King et al., "Insertion mutagenesis of embryonal carcinoma cells by retroviruses," Science 228:554–558, 1985. The random integration of genes into the DNA of mammalian cells, in addition to causing mutations, also causes problems in the expression of the wild type gene. As is known to those skilled in the art, wild type genes situated at their proper loci are usually expressed only in a pattern specific for that particular gene. Thus, for example, certain genes are expressed in an animal's liver and not in its brain. However, when wild type genes are randomly integrated into the DNA of mammalian cells, they are generally not expressed at all and, in those cases where they are expressed, they are usually not expressed in the proper pattern.

Furthermore, in addition to causing mutations and improper expression or no expression, the random integration of wild type genes into the DNA of mammalian cells will not remove the disease-causing gene from the cell. Since such a disease-causing gene sometimes is dominant, the random integration of the wild type genes into such DNA is at best ineffective. There has been a long-felt need for a process for specifically removing the disease-causing gene from the DNA of a cell and replacing it with a wild type gene at a sufficiently high frequency so that the diseased cell will be cured. The slime mold Dictyostelium discoideum is a model system for developmental genetics since for part of its life cycle it is a unicellular amoebae and as such it is very well amenable to molecular biology approaches.

However, one of the most important problems with the development of Dictyostelium as research tool is that cloning by functional complementation with plasmid-borne genomic libraries has not been successful for developmental genes where direct selection cannot be applied. Transposon tagging has been successfully used in other organisms such as Drosophila and Caenorhabditis for the isolation of developmental genes. However, because of the lack of the ability to mobilize transposable elements, this strategy is not possible in Dictyostelium. A method for insertional mutagenesis would be a breakthrough for developmental biology with Dictyostelium and many other organisms.

About fifteen years ago some experiments were reported which allegedly, with the use of a restriction enzyme, incorporated a certain gene fragment into a bacterial plasmid. In an article by Shing Chang and Stanley N. Cohen entitled "In vivo site-specific genetic recombination promoted by the EcoRI restriction endonuclease" (Proceedings of the National Academy of Science U.S.A., Volume 74, No. 11, pp. 48–11–4815, November, 1977), a claim was made that "The experiments reported here indicate that the EcoRI endonuclease can function in vivo in conjunction with the *E.coli* DNA ligase to accomplish site-specific genetic recombination."

Since 1977, to the best of applicant's knowledge, no reports have appeared in the literature confirming the results reported in the Chang et al. reference, no reports have appeared in the literature utilizing the Chang et al. process for other genetic manipulations, and no comment has appeared in the literature regarding the Chang et al. reference or process. In fact, the experiments of the Chang et al. publication do not appear to be reproducible. Applicant has attempted to reproduce the results reported in the Chang et al. publication at least three times, to no avail. Applicant has been informed that other researchers have also unsuccessfully attempted to reproduce the Chang et al. results.

About 700,000 new cases of cancer affect North Americans each year. It is estimated that about 70 to 90 percent of these new cases of cancer are linked to environmental carcinogens. Epidemiologists estimate that at least about 70 percent of human cancers would be preventable if the main risk and antirisk factors could be identified. One epidemiological example of this phenomenon is colon and breast cancer. These are among the major types of cancer in the United States, but they are quite rare among Japanese living in Japan. However, Japanese living in the United States have a relatively high incidence of this disease.

There are in excess of about 60,000 chemicals in commercial production. Over 400,000 new organic compounds are synthesized every year, and at least 1,000 of them each year will eventually be introduced into economic use. There is a need to be able to determine which of these new compounds will cause cancer. However, it is difficult to predict without testing whether any particular chemical will cause cancer.

The most reliable means for determining whether a particular compound is carcinogenic is a long term assay, which generally is based on the experimental assessment of the potential of the substance to induce tumors in rodents. Long term assays usually take from 2 to 4 years to conduct, and they are relatively expensive. Because of the time and/or the expense involved, it is not feasible to conduct long term assays in many situations, especially where one is seeking a preliminary indication as to whether to proceed with the development of a particular substance.

The need for relatively fast and inexpensive means for preliminarily evaluating the cancer-causing potential of new chemicals has led to the development of many short term assays; some of these short term assays are described in column 4 (lines 13-44) of U.S. Pat. No. 4,701,406. The most widely known of these short-term assays is the Ames Assay. This Assay is based upon the assumption that carcinogens will cause the genetic reversion of certain mutant strains of the bacteria *Salmonella typhimurium*. In other words, the mutant strains revert to their normal form in the presence of mutagens. A description of the Ames Assay may be found, e.g., in an article by Ames et al., "Methods for Detecting Carcinogens and Mutagens with the Salmonella/ Mammalian-Microsome Mutagenicity Test," Mutation Research, vol. 31 (1975), pp. 347-364.

One disadvantage of the Ames Assay is that it cannot evaluate compounds which are bactericidal. Yet another disadvantage of the Ames Assay is that many classes of carcinogenic compounds consistently show poor responses in this assay and also in mammalian cell genotoxic assay systems. Thus, as is disclosed at column 4 of U.S. Pat. No. 4,701,406, the Ames Assay is not very useful for evaluating certain metals, steroid hormones, and chlorinated hydrocarbons which, although they are known to be carcinogens, give very poor or no responses.

One of the major problems with the Ames Assay is that, although it is useful for evaluating certain mutagenic compounds, it is not generally useful for evaluating carcinogenic compounds which are not mutagenic. See, for example, McCann et al., "Detection of Carcinogens as Mutagens in the Salmonella/Microsome Test: Assay of 300 Chemicals, Proc. Nat. Acad. Sci. USA, vol. 72, No. 129 (1975), pp. 5135-5139. Also see McCann et al., "Detection of Carcinogens as Mutagens in the Salmonella/Microsome Test: Assay of 300 Chemicals Discussion," Proc. Nat. Acad. Sci. USA, vol. 73, No. 3 (1976), pp 950-954.

Short term tests involving mutation and recombination assays with the yeast *Saccharomyces cerevisiae* have been developed. However, these yeast assays are only able to detect about 74 percent of the known carcinogens as being positive. See, for example, an article by Zimmermann et al. appearing in Mutation Research, vol. 133 at pages 199-244 (1984).

The prior art teaches the use of both the Ames Assay and the aforementioned yeast assay in combination, but even the use of both of these assays fails to detect many nonmutagenic carcinogens. See, e.g., the aforementioned article by Zimmermann et al.

Not only do the prior art short-term tests fail to show positive results with many known carcinogens, but they also usually fail to indicate whether a prospective carcinogen will cause genome rearrangement. There is a substantial body of literature indicating that compounds which cause genome rearrangement might cause cancer. Thus, it has been shown that the excision of retroviruses from genomes can cause cancer; see Bishop, Ann. Rev. Biochem. 52:301-354 (1983) and Bishop, Cell 42:23-38 (1985). Thus, it has been shown that amplification of specific human DNA sequences up to 120 times are associated with cancer; see Montgomery et al., Proc. Natl. Acad. Sci. USA 80:5724-5728 (1983) and Schwab et al., Proc. Natl. Acad. Sci. USA 81:4940-4944). Thus, it has been shown that immunoglobulin class switching in B lymphocyte differentiation is associated with cancer; see Brown et al., Proc. Natl. Acad. Sci. USA 82:556-560 (1985), Korsmeyer et al., Proc. Natl. Acad. Sci. USA 80:4522-4526 (1983), and Cleary et al., Proc. Natl. Acad. Sci. USA 81:593-597 (1984). Thus it has also been shown that rearrangements involving the T Cell receptor gene are associated with cancer; see Flug, Proc. Natl. Acad. Sci. USA 82:3460-3464 (1985) and Minden et al. Proc. Natl. Acad. Sci. USA 82:1224-1227 (1985). Thus, it has also been shown that amplification preceded by mutation of a gene is associated with cancer; see, e.g., Fujita, Proc. Natl. Acad. Sci. USA 82:3849-3853 (1985). Thus, it has also been shown that deletions in recessive oncogenes are associated with carcinogenesis such as retinoblastoma; see, e. g., Hansen and Cavanee, Cell 53:172-173 (1988), see also, Ponder, Nature 335:400-402 (1988). Leukemia may be caused by translocations. The role of genome rearrangement in carcinogenesis has also been discussed in more general terms in Klein, Nature 294:313-318 (1981), Pall, Proc. Natl. Acad. Sci. USA 78:2465-2468 (1981), Cairns, Nature 289:353-357 (1981), Wintersberger, Naturwissenschaften 69:107-113 (1982) and Haluska et al., Annu. Rev. Genet. 21:321-345 (1987).

Illegitimate recombination events are those that join two DNA molecules (or two non-contiguous parts of a single DNA molecule) without the requirement for sequence identity. In general, it is difficult to distinguish illegitimate recombination events from those that involve very limited sequence identity. These events are likely to be an important cause of chromosome rearrangements which in turn are associated with the aforementioned cancers. In a number of genetic defects caused by genomic rearrangements, either no homology or very limited homology has been detected at the junctions of the rearrangements (see e.g. a review by Meuth, M. (1989) entitled "Illegitimate recombination in mammalian cells" published in a book entitled "Mobile DNA" edited by Berg, D. E. and Howe, M., published by ASM Publication, Washington D.C.) Another review directly concerns the involvement of illegitimate recombination in carcinogenesis; see Duesberg et al. 1989, in a publication entitled "Cancer genes by illegitimate recombination," published in the Annals of the New York Academy of Sciences, New York, volume 567 on pages 259 to 273. Similar "illegitimate" recombination events have also been characterized in bacteria; see e.g. a review by Ehrlich, S. D. (1989) entitled "Illegitimate recombination in bacteria" published in a book entitled "Mobile DNA", edited by D. E. Berg and M. Howe (published by ASM Publications, Washington D.C. on pages 799-832).

Illegitimate recombination in *Saccharomyces cerevisiae* was first shown by Schiestl and Petes (1991) in a publication entitled "Integration of DNA fragments by illegitimate recombination in *Saccharomyces cerevisiae*", published in Proc. Natl. Acad. Sci. USA, vol. 88, pages 7585-7589. Illegitimate recombination may be used for insertional mutagenesis in yeast. In one preferred embodiment of said process functional or nonfunctional elements may be used to perform insertional mutagenesis of the yeast genome. Most mutations in yeast are induced by chemical mutagens or treatment with ultraviolet light. There is evidence that all genes are not equally susceptible to these mutagens. Thus, mutagenesis by insertion of selectable genes may identify different genes than those identified by traditional mutagenesis procedures. There are at present two types of procedures that have been used for insertional mutagenesis. One procedure involves making insertions of transposons into recombinant plasmids containing yeast DNA in *Escherichia coli*; see e.g. a publication by Seifert et al. in 1986, published in Proc. Natl. Acad. Sci. USA volume 83 on pages 735 to 739. The disadvantage of this method is its very labour intensive nature. The second method of insertional mutagenesis is to induce transposition of a plasmid borne Ty element as described in a publication by Garfinkel et al. 1988 published in Genetics volume 120 on pages 95 to 108. This procedure has been used to isolate insertions in a number of different loci. One problem with this procedure is the striking non-randomness in insertion frequency. At both the LYS2 and the URA3 loci, Ty insertions have strong preference for the 5' end of the gene (as described in a publication by Natsoulis et al. 1989 published in Genetics 123 on pages 269 to 279). Furthermore, use of this method by J. Boeke and collaborators to study integration events in chromosome III of Saccharomyces cerevisiae has shown that only 4.2% of the insertions disrupted an open reading frame, in spite of the fact that 70% of chromosome III is composed of open reading frames.

In addition to making mutations, insertion elements can be used to identify promoter and open-reading frames. For example, Huisman et al. 1987 (published in Genetics 116 on pages 191 to 199) constructed a transposable element that contained a beta-galactosidase gene that lacked a promoter and translational start, a URA3 gene and a $kan^R$ gene. When this element integrated into the chromosome near a yeast promoter in the correct reading frame, functional beta-galactosidase was produced, as determined by the blue color on medium containing X-gal. Since the procedure to construct these insertions uses the above mentioned method by Seifert et al., this method is extremely labour intensive.

In many organisms insertional mutagenesis can be accomplished by induction of transposition events. Examples can be found, e.g., in bacteria; see Tucker et al. U.S. Pat. No. 5,102,797, Ty elements in yeast (see above), P-elements in Drosophila, see Rubin et al. U.S. Pat. No. 4,670,388, and Ti plasmid mutagenesis in dicotyledonous plants, see Schilperoort et al., U.S. Pat. No. 4,693,976.

However, in mammalian organisms the study and use of "mammalian transposition has been hampered tremendously by the lack of an experimental system in which transposition can be induced and observed directly"; see an article by P. Deininger entitled "Induction of DNA rearrangement and transposition" published in Proc. Natl. Acad. Sci. USA volume 90 on pages 3780–3781. The same is true for many other cells, like Dictyostelium. Hence a system for insertional mutagenesis in mammalian cells would be extremely useful.

Experimental genetics and molecular biology in diploid organisms is severely hampered by the fact that most mutations caused by a mutagenic method will be recessive and thus do not show any phenotype in the same generation or in the next generation after mutagenesis. Hence a process to use an insertional mutagenesis process to insert a gene selectively into expressed target genes which in turn causes a conditional mutation of the homologous gene on the other homolog would be a milestone in the application of molecular biology to mammalian genetics.

Another use of illegitimate recombination is to construct genome rearrangements. In general, naturally-occurring genome rearrangements are rarely detected in yeast. Some genome rearrangements have been constructed by selecting for recombination between repeated genes. The existing procedures for generating chromosomal rearrangements are tedious; however, genome rearrangements are useful for a large number of genetic studies.

It is an object of this invention to provide a process for insertional mutagenesis, promoter and open reading frame searches, insertions of DNA fragments specifically into expressed genes thereby causing a conditional mutation in the other allele of that gene and the construction of chromosomal rearrangements for genomic studies and for the identification of genes involved in illegitimate recombination in yeast cells.

It is another object of this invention to provide a process for insertional mutagenesis, promoter and open reading frame searches, insertions of DNA fragments specifically into expressed genes thereby causing a conditional mutation in the other allele of that gene and the construction of chromosomal rearrangements for genomic studies and for the identification of genes involved in illegitimate recombination in Dictyostelium cells.

It is another object of this invention to provide a process for insertional mutagenesis, promoter and open reading frame searches, insertions of DNA fragments specifically into expressed genes thereby causing a conditional mutation in the other allele of that gene and the construction of chromosomal rearrangements for genomic studies and for the identification of genes involved in illegitimate recombination in mammalian cells.

It is another object of this invention to provide a process which can be used to target genes to specific positions in the DNA of yeast cells.

It is another object of this invention to provide a process which can be used to target genes to specific positions in the DNA of Dictyostelium cells.

It is yet another object of this invention to provide a process which can be used to target genes to specific positions in the DNA of mammalian cells.

It is yet another object of this invention to provide a process to construct hybrid DNA, hybrid proteins and hybrid enzymes with novel or improved properties by fusing the DNA fragments of heretofore separate fragments of DNA together by illegitimate recombination and/or restriction enzyme mediated recombination.

It is yet another object of this invention to provide a process for inserting

It is yet another object of this invention to provide a short-term assay system which can be used to evaluate many bactericidal compounds.

It is yet another object of this invention to provide a short-term assay which can be used to evaluate many non-mutagenic compounds which are carcinogenic and which do not show positive results in the prior art Ames Assay and yeast assay system.

It is yet another object of this invention to provide a short-term assay system which can be used to evaluate many compounds or compositions which cause illegitimate recombination which gives rise to genome rearrangements.

DISCLOUSURE OF INVENTION

In accordance with this invention, there is provided a process for targeting genes to specific positions in the DNA of yeast cells, for insertional mutagenesis, promoter and open reading frame searches, insertions of DNA fragments specifically into expressed genes thereby causing a conditional mutation in the other allele of that gene and for the construction of chromosomal rearrangements for genomic studies. In the first step of this process, a yeast plasmid is digested with a restriction enzyme in order to introduce at least one restriction enzyme cut into the plasmid. In the second step of the process, the digested plasmid is, without or together with a restriction enzyme, incubated with yeast cells to cause a transformation reaction. In the third step, yeast cells are contacted with media which tend to select those yeast cells containing the plasmid or some part(s) thereof.

In accordance with this invention, there is also provided another process for targeting genes to specific positions in slime mold DNA. The steps are similar to the ones mentioned above for yeast cells.

In accordance with this invention, there is also provided another process for targeting genes to specific positions in mammalian DNA. The steps are similar to the ones mentioned above for yeast cells.

In accordance with this invention, there is also provided another process for screening an agent in order to determine whether such agent increases the frequency of illegitimate recombination in living matter.

In the first step of this process involving illegitimate recombination, there is provided a viable species of Saccharomyces cerevisiae yeast which comprises a free or in the genome integrated plasmid or DNA fragment which does not show any extended sequence identity to the genomic DNA of that particular strain. This plasmid or DNA fragment contains DNA sequences selected from the group consisting of functional or nonfunctional genetic elements; under ambient conditions these genetic elements recombine with the genomic DNA of the strain or with another plasmid or DNA fragment by one or more mechanisms which require no extended homology.

In the second step of this process, the viable species of yeast is exposed to the agent to be tested. This second step applies only if the process is used to determine the potential carcinogenic effect of agents. Otherwise this second step may be ommitted. Thereafter, it is plated onto a growth medium which, after the exposed or nonexposed yeast species grows upon it, facilitates the identification of those cells which have undergone said illegitimate recombination events.

In the last step of the process, the extent to which the exposed species of yeast has undergone illegitimate recombination is determined or the illagitimate recombination events are retrieved and may be further analyzed for all other uses.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 1 is a schematic of a functional URA3 gene of Saccharomyces cerevisiae, a preferred recombination substrate for illegitimate integration or restriction enzyme mediated recombination which is selectable for;

DEFINITION OF TERMS

Figure 1:
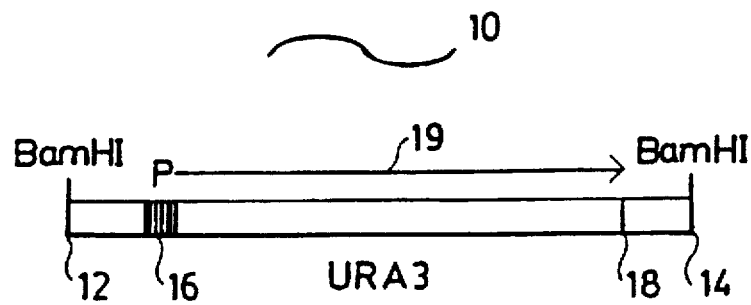

The first portion of this part of the specification contains a definition of terms. Many of the terms used in this patent are well known to those skilled in the art and are used, e.g., in applicant's U.S. Pat. No. 4,997,757. Chapters 7, 17, and 19 a book by U. Good enough entitled "Genetics" Third Edition, (Saunders College Publishing, New York, 1984) discusses genetic alterations. Many of the terms used in this specification are defined in the Good enough book and also in a text by W. Ralph Singleton entitled "Elementary Genetics", Second Edition (American Book Company, New York, 1962), at pages 537–559. Additionally many of the terms used in this specification are also defined in a book by Benjamin Lewin entitled "Genes IV" published by Oxford University Press, New York, NY. Additionally many of the terms used in this specification are also defined in a book by James D. Watson et al. entitled "Recombinant DNA" published by Scientific American Books, New York, N.Y. Furthermore, many of the terms used in this specification are also defined in a book by C. Morris entitled "Academic Press Dictionary of Science and Technology" published by Scientific Academic Press, New York, New York. The following terms may be used hereinafter:

Allele: Any of one or more alternative forms of a given gene. They occur by mutation, where deletions, substitutions, or insertions have altered the original specific sequence of nucleotides.

Crossing over: Crossing over is reciprocal recombination joining different homologous DNA molecules so that genes combined as A-B and a-b are now arranged A-b and a-B. Crossing over might result from the breaking and reunion between two homologous chromosomes. Homologs are chromosomes that are sufficiently similar to pair during meiosis.

Coding region: The coding region of a gene is discussed on pages 36 to 46 of the aforementioned book by Watson et al. The coding region of a gene is the DNA sequence which defines the amino acid sequence of the corresponding gene product. A gene product is the protein produced after transcription of a gene and after translation of the transcribed RNA. Transcription is the formation of an RNA copy corresponding to the DNA copy of that gene by RNA polymerase. Translation is the formation of a peptide or protein when the RNA copy is translated into a defined amino acid sequence at the ribosomes. The amino acid sequence is defined by the nucleotide sequence of the DNA.
Exon: The portion of the DNA sequence in a gene that contains the codons that specify the sequence of amino acids in a polypeptide chain, as well as the beginning and the end of the coding sequence.
Gene: The unit of hereditary function. It is a DNA (deoxyribonucleic acid) sequence which encodes a functional protein.
Gene convesion: Gene conversion is the nonreciprocal transfer of information in terms of DNA sequence from one DNA double strand to another so that, for example, genes ABC and abc are converted to AbC and abc. Gene conversion is discussed on pages 561–565 of a book by U. Good enough entitled "Genetics" Third Edition, (Saunders College Publishing, New York, 1984). Genome rearrangement: Genome rearrangement is another genetic alteration. A genome is a complete haploid set of chromosomes. A haploid organism is a viable structure having a single set of chromosomes; by comparison, a diploid organism has two sets of chromosomes. A genome rearrangement is any genetic event which rearranges the order of genes within a haploid genome or between a haploid genome and other genetic elements, thereby creating a new environment for particular genes either on a different chromosome or on the same chromosome in a different position. Genome rearrangements include, e.g., deletions, translocations, gene amplification, insertions and rearrangements within genes. Deletions identify a loss of any DNA sequence from the genome. A translocation involves the interchange of the position of sequences on nonhomologous chromosomes. Gene amplification is a multiplication of a DNA sequence whereby, e.g., a gene sequence is duplicated, triplicated, etc. Insertions insert DNA sequences of a plasmid virus or DNA fragment into the genome.
Homology: The degree of identity between the nucleotide sequences of two nucleic acid molecules or the amino acid sequences of two protein molecules. Although sequence determination is the ultimate test of homology, useful estimates can be provided by either DNA-DNA or DNA-RNA hybridization. Illegitimate Recombination: Recombination events in the absence of substantial homology between the two recombining alleles. Illegitimate recombination gives rise to genome rearrangements. Illegitimate recombination is discussed in the above mentioned publication by Ehrlich, S. D. (1989) entitled "Illegitimate recombination in bacteria" published in a book entitled "Mobile DNA", edited by D. E. Berg and M. Howe, published by American Society for Microbiology Publications, Washington D.C. on pages 799–832.
Integration: The recombination process which inserts a small DNA molecule into a larger one.
Intrachromosomal recombination: Recombination within one chromosome, either intrachromatid (within one chromatid) or between sister chromatids. As is known by those skilled in the art, the term chromatid refers to one of the two parts of a chromosome which exist after replication, there being one DNA double helix before replication, and two identical DNA double helices after replication, the basis elements of the two chromatids, attached at the centromere of a replicated chromosome; intrachromosomal recombination often causes a genetic endpoint. Interchromosomal recombination is recombination between homologous chromosomes in a diploid cell, and it also often causes a genetic endpoint.

Intron: An apparently nonfunctional segment of DNA, which is transcribed into nuclear RNA but is then removed from the transcript and rapidly degrades.
Mutant: A genetic alteration of the wild-type which usually makes the wild-type allele nonfunctional.
Plasmid: An extrachromosomal element capable of independent replication.
Recombination: The joining together of two DNA molecules which theretofore had not been joined.
Promoter: A promoter is discussed on page 45 of the aforementioned book by Watson et al. The promoter is a DNA sequence in front of the coding region of a gene that RNA polymerase binds to and thus initiates transcription at the start site. Thus the promoter is required for expression of a functional gene, such as the URA3 gene. If the promoter of a gene is lacking, the gene is not expressed and no gene product is made and it falls therefore under the definition of the nonfunctional alleles.
Restriction Enzyme: The term "restriction enzyme," also commonly referred to as "restriction endonuclease," refers to a number of enzymes, derived from a wide range of prokaryotes, that all cleave double-stranded DNA molecules. See, for example, U.S. Pat. No. 4,064,011, 4,746,609, 4,808,525, and 4,840,901, the disclosures of each of which is hereby incorporated by reference into this specification. Also see page 207 of John M. Walker et al.'s "The Language of Biotechnology: A Dictionary of Terms" (American Chemical Society, Washington, D.C., 1988).
Restriction enzyme mediated recombination: The joining together of two DNA molecules which theretofore had not been joined catalyzed by a restriction enzyme.
Sequence homology: This term refers to DNA sequence homology and defines regions of DNA sequence which are the same at different locations of the genome, or between different DNA molecules such as between the genome and a plasmid or DNA fragment. As those in the art are aware, the extent of perfect homology is important as definition for homologous sequences. Perfect homology entails the same sequences over some distance in the DNA. As those in the art are aware the length of the distance of perfect homology is important. Homologous recombination in yeast requires homology at the point of interaction between the recombining DNA molecules, see e.g. a publication entitled "Recombination in Yeast" by T. Petes et al. (in a book entitled "The Molecular Biology of the Yeast Saccharomyces" edited by E. Jones et al. 1992 Cold Spring Harbor Laboratory Press, Cold Spring Harbor, N.Y.) The point of interaction between the recombining molecules in yeast is at the sequences flanking the double strand break during integration of a DNA fragment or plasmid or at the sequence where the novel recombination joint is created when intragenomic sequences recombine. Since the genome of yeast contains approximately $2.3 \times 10^7$ basepairs, any randomly chosen sequence of 12 basepairs in length will occur on a random bases only about once per yeast genome. In addition with oligonucleotides of 15 basepairs in length, no homologous recombination events were detected, see a publication by Moerschell et al., 1988, Proc. Natl. Acad. Sci. USA, volume 85 pages 524 to 528. The junction sequences have been determined from about 30 illegitimate integration events: see a publication by Schiestl and Petes 1991 entitled "Integration of DNA fragments by illegitimate recombination in yeast" published in Proc. Natl. Acad. Sci. USA vol. 88 pages 7585 to 7589 and results presented later in this specification. In none of the 30 cases so far analyzed at the DNA sequence level were 15 basepairs of homology found at the junction, therefore we may define illegitimate recombination in this specification as less than 15 basepairs of perfect homology at the point of interaction of the recombining DNA molecules. As those in the art are aware this definition will exclude homologous recombination (substantially more than 15 basepairs of almost perfect homology at the point of interaction of the two recombining DNA molecules is required).

Splicing: As used in this specification this term is equivalent to the term RNA splicing as defined in the aforementioned Academic Press Dictionary: a processing procedure in which two exons, or coding sequences, are joined together in a eukaryotic mRNA after excision of the intervening introns; used to produce a mature RNA molecule.

Wild-type: The usual or non-mutant form of a gene or organism. This term was originally meant to denote the form in which the organism was found in nature. It has come to have a more specialized meaning, referring to the genetic constitution of an organism at the start of a program of mutagenesis.

Yeasts: Fungi that are usually unicellular for part of their life history, but may also form pseudomycelium or short lengths of true mycelium. The common method of vegetative reproduction of many yeasts is by budding.

BEST MODE FOR CARRYING OUT THE INVENTION

The present invention provides a process for insertional mutagenesis, promotor and open reading frame searches, for insertions of DNA fragments specifically into expressed genes thereby causing a conditional mutation in the other allele of that gene, for the construction of chromosomal rearrangements for genomic studies and for the identification of genes involved in illegitimate recombination. The present invention also provides a short term assay for identifying potential carcinogens. This short term assay selects for a genetic endpoint, namely illegitimate recombination, which is frequently associated with cancer.

In one process of this invention, a genus of the yeast *Saccharomyces cerevisiae* with certain specified properties is used in conjunction with a specified medium to select for illegitimate recombination events or for restriction enzyme mediated recombination events. The yeast used in this process must undergo illegitimate recombination between DNA sequences without extended DNA sequence identity and thus cause genome rearrangement which must be selectable or otherwise identifiable.

The yeast *Saccharomyces cerevisiae* has been extensively used in the field of classical genetics. Because of its properties, it is extremely useful in molecular biology research. These properties include an extremely high frequency of homologous recombination, which allows one to readily make specific constructions in the genome. Thus, for example, one can readily reintroduce certain in vitro constructed altered genes into its genomic position.

Not every species of said yeast works in the process of this invention. The process utilizes those viable species of *Saccharomyces cerevisiae* which can be transformed with DNA which does not show any extended sequence identity with the genomic DNA of the yeast strain or which contains a DNA fragment on a plasmid or integrated into the genome which does not show any extended sequence identity to the genomic DNA of the yeast strain. Thus, by way of illustration, such species of yeast may contain a deletion of the URA3, or the LEU2, TRP1, LYS2, ADE2 or any other gene. Thus, by way of illustration, yeast chromosomes normally contain one URA3 gene. In order to be used for one preferred embodiment in the process of this invention, the yeast chromosomes should be deleted for the entire open reading frame of the URA3, LEU2, TRP1, LYS2, ADE2 gene or the like removing most of the homology so that homologous recombination does not occur at a frequency interfering with selection for the illegitimate or restriction enzyme mediated recombination events which are the objects of this specification.

By way of illustration and not limitation, the transforming DNA used in conjunction with said process may contain functional elements, such as the entire URA3, LEU2, TRP1, LYS2, ADE2 gene or the like, such that no homology exists between the transforming DNA and the genome (which has been deleted for these genes) of said yeast strain.

In another preferred embodiment, the transforming DNA used in conjunction with said process may contain nonfunctional elements, such as fragments of the URA3, LEU2, TRP1, LYS2, ADE2 genes or the like, that lack their own promoter, including or not including the first several amino acids of the gene product, such that no homology exists between the transforming DNA and the genome (which has been deleted for these genes) of said yeast strain. In this preferred embodiment, the promoterless gene is rendered functional only after illegitimate recombination with the genome of said yeast strain such that the transforming DNA fragment acquires a functional promoter from the genomic DNA of said strain. Therefore, the functional URA3, LEU2, TRP1, LYS2, ADE2 genes or the like are exclusively the result of illegitimate recombination events leading to integration of the promoterless fragment into the genome of said strain.

In another preferred embodiment of said process functional or nonfunctional elements may be used as long as they do not show any extended homology to the genome of said yeast strain and as long as they are selectable for either self sufficient (functional elements) or after integration into the genome whereby they may acquire a promoter as described above (nonfunctional elements). By way of illustration and not limitation for this purpose the bacterial neomycin gene can be used which confers resistance to G418 in yeast. By comparison normal yeast strains are sensitive to G418. The ability to select for the neomycin gene in yeast is described in a publication entitled "Expression of a transposable antibiotic resistance element in Saccharomyces" by Jimenez et al. (1980) published in Nature 287 on pages 689 to 691. By way of illustration and not limitation another gene useful for this embodiment is the hygromycin B gene which produces resistance to hygromycin B in yeast. By comparison normal yeast strains which do not contain the hygromycin B resistance gene are unable to grow in the presence of 200 microgram of hygromycin B per milliliter of growth medium. The usefulness of the hygromycin B gene in yeast is described in a publication entitled "Hygromycin B resistance as dominant selectable marker in yeast" by Kaster et al. (1984) published in Current Genetics volume 8 on pages 353 to 358.

FIG. 1 illustrates construct 10, a 1.1 kilobase pair long DNA fragment with Ba HI ends containing the entire URA3 gene used for transformation of the yeast strain deleted for the URA3 gene. Construct 10 exists as a 1.1 kilobase pairs long fragment flanked with either BamHI sites, HindIII sites or EcoRI sites at points 12 and 14. A plasmid PM20 containing construct 10 as a BamHI fragment is available to those skilled in the art and has been constructed by Sue Jinks-Robertson (Emory University) and Martin Kupiec (Tel Aviv University); it has been described by R. Schiestl and T. Petes in the aforementioned paper published in Proc. Natl.

Acad. Sci. USA 1991 vol. 88 on pages 7585 to 7589. As those skilled in the art are aware, construct 10 flanked by HindIiI sites can also be used in applicant's process and is contained in one of the most commonly used and widely available vectors containing the URA3 gene. Thus, for instance, plasmids YIp5, YEp24 disclosed in a paper by Botstein et al. 1979 in Gene volume 8 on pages 17 to 24, and many other cloning vectors, contain the URA3 gene and can be obtained from most laboratories working on yeast molecular biology. Fragment 10 contains the promoter P, point 16 of the URA3 gene and the adjacent coding region up to point 18 of the URA3 gene. As those skilled in the art are aware, this DNA fragment contains all the information needed to be transcribed into the RNA and thereafter to be translated to confer uracil prototrophy to the cells. The direction of transcription in FIG. 1 is indicated by arrow 19.

The fragment of FIG. 1 is only one of many within the scope of this invention which do not show any extended homology to the genome of the yeast strain. Thus, by way of illustration and not limitation, fragment 10 may be replaced by the HIS3, TRP1, URA3, LYS2, ADE2 genes as long as the genome of the respective strains have been deleted for these genes.

Figure 2:
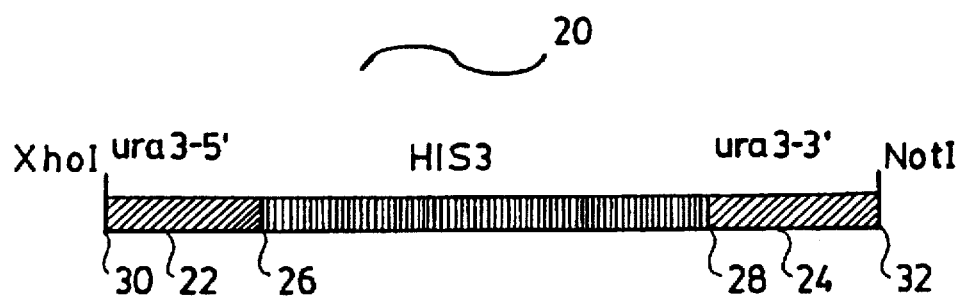
FIG. 2 is a schematic of one of the possible deletion alleles to delete the entire open reading frame of the URA3 gene, including sequences at the junctions so that all homology to the URA3 fragment shown in FIG. 1 is removed from the genome of the recipient strain. Without limitation this deletion allele may be used for constructs shown in FIGS. 1, 3, 4 and 5.

FIG. 2 illustrates construct 20, which is used to delete the URA3 gene from the yeast strain used in applicant's procedure. Strain RSY12 can be used in applicant's process which was deleted for all sequences of the URA3 gene shown in FIG. 1. Referring to FIG. 2 construct 20 consists of the HIS3 fragment containing the entire HIS3 gene flanked by DNA sequences 22 ura3-5' and 24 ura3-3'. The HIS3 gene is also readily available to those skilled in the art, it is for instance contained on plasmid pSZ515 which is also readily available; its construction is described in a publication by Orr-Weaver et al. entitled "Yeast transformation: a model system for the study of recombination", Proc. Natl. Acad. Sci. USA, 78:6354–6358, 1981. It should be noted that the Orr-Weaver reference also discloses the preparation of other plasmids. The sequences ura3-5' and ura3-3' are taken from the 5' and 3' flanking regions respectively of the genomic URA3 locus. DNA sequences 5' and 3' of the URA3 gene have been cloned by M. Rose et al. 1984 and published in a paper entitled "Structure and function of the URA3 gene: expression in *Escherichia coli*" published in Gene volume 29 on pages 113 to 124. As known to those skilled in the art these sequences are freely available. The fragment containing construct 10 of FIG. 1 was deleted and replaced by the HIS3 gene. Referring again to FIG. 2 construct 20 can be obtained by digesting plasmid pJL202 with the restriction enzymes XhoI at point 30 and NotI at point 32 by means well known to those skilled in the art. Plasmid pJL202 is freely available and has been constructed by Joachim Li in Jef Boeke's laboratory. Plasmid pJL202 has been obtained from Jef Boeke at Johns Hopkins University, Department of Molecular Biology and Genetics, 725 N. Wolfe Street, Baltimore, Md. 21205. Plasmid pJL202 has been constructed by starting with a plasmid containing the aforementioned URA3 large fragment. A 1.1 kb HindIII fragment containing the entire construct 10 was deleted from this plasmid by digestion with HindIII. Furthermore a commercially available SmaI linker, available, e.g., from New England Biolabs, 32 Tozer Road, Beverly, Mass. was ligated into the single HindIII site of this plasmid. Thereafter this plasmid was digested with SmaI and an EcoRI-BamHI fragment containing the aforementioned HIS3 gene was cloned into the SmaI site. To clone the URA3 fragment into the SmaI site the sticky ends of the EcoRi and BamHI sites were filled with Klenow fragment of DNA polymerase and DNA ligation was carried out. All these procedures are well known to those skilled in the art. The product of this construction is plasmid pJL202 which was used to construct strain RSY12 used in applicants process. Thus after digestion of plasmid pJL202 with XhoI and NotI strain OD5 was transformed with the digestion mixture and HIS+ colonies were isolated on medium lacking histidine. Strain OD5 is freely available and has been obtained from Walter Spevak in the laboratory of Helmut Ruis, Department of Biochemistry, University of Vienna, Wahringerstrasse 49, 1090 Vienna, Austria. The resulting HIS+ colonies were screened for their uracil phenotype and one URA- colony was named RSY12 and was used for one preferred embodiment of applicant's process. This step of construction of strain RSY12 is also published in the aforementioned paper by Schiestl and Petes, published in Proc. Natl. Acad. Sci. USA 1991 vol. 88 on pages 7585 to 7589. As those in the art are aware other means to delete the URA3 gene can also be used. Alternative constructs 20 may contain the LEU2, TRP1, URA3, LYS2, ADE2 genes or the like instead of the HIS3 gene.

By way of illustration and without limitation, another way to delete the URA3 gene is by construction of the URA3 deletion first and then transformation of the yeast strain selecting on medium containing 5 fluoroorotic acid against the URA3 gene. For instance plasmid pDB3 which has been constructed, is freely available from Dan Gietz, Department of Human Genetics, University of Manitoba, 770 Banntyne Ave, Winnipeg, Manitoba, Canada R3E 0W3. Plasmid pDB3 contains the 5.5 kilobase long BamHI fragment with the URA3 gene as described in a paper by M. Rose et al. 1984 published in Gene volume 29 on pages 113 to 124. Plasmid pDB3 was constructed in the following way. Sequences 5' and 3' of the 1.1 kilobasepair long HindIII fragment containing the URA3 gene of the aforementioned Rose et al. paper including the 1.1 kilobasepair long HindIII fragment were cloned. The cloning of this fragment has been described in detail in a publication by Gietz and Schiestl entitled "Applications of high efficiency lithium acetate transformation of intact yeast cells using singlestranded nucleic acids as carrier" published in Yeast (1991) volume 7 on pages 253–263.

Yeast genomic libraries were constructed as follows. DNA was extracted from a 100 milliliter stationary culture of the yeast strain D7 using the method of Cryer et al. (1975) published in an article entitled "Isolation of yeast DNA" published in Meth. Cell. Biol. 12 on pages 39–44. The yeast genomic DNA obtained was partially digested with the restriction enzyme MboI. The optimal condition for partial digestion of yeast DNA were determined by the procedure described on page 282 of a book by Maniatis et al. (1982) entitled "Molecular Cloning: A laboratory manual", published by Cold Spring Harbor Laboratory Press, Cold Spring Harbor, N.Y. Once determined the reaction was scaled up to digest approximately 50 microgram of genomic DNA.

The purification of random 10–12 kilobasepair long and 15–19 kilobasepair long partially digested DNA fragments from an agarose gel by electrophoresis onto dialysis membrane was carried out using a modification of the method of Girvitz et al. (1980) entitled "A rapid and efficient procedure for the purification of DNA from agarose gels" published in Analytical Biochemistry volume 106 on pages 492–496. The partially digested DNA was electrophoresed with BRL high molecular weight standards (obtained from Life Technologies, Inc. of 8400 Helgerman Court, Gaithersburg, Md. 20877) as size markers in a 0.45% agarose Tris acetate EDTA gel in the absence of ethidium bromide at 4 degrees celsius. The gel was stained with ethidium bromide and DNA of the desired size electrophoresed onto a piece of Whatman 3MM paper:dialysis membrane inserted into an incision at the lower size limit. The Whatman 3MM paper:dialysis membrane was placed in a punctured 400 microliter microcentrifuge tube, held in a decapitated 1.5 milliliter tube and the DNA was eluted by washing with three 100 microliter aliquots of band elution buffer (10 millimolar Tris-HCl, pH 7.5, 200 millimolar sodium chloride, one millimolar EDTA, 0.2 percent SDS). Excessive centrifugation during the elution step dramatically reduced the DNA yield. The collected supernatant was extracted once with phenol chloroform and DNA ethanol precipitated. The yield of sized randomly digested MboI DNA fragments from 50 microgram of geniomic DNA ranged between 2 and 5 microgram. Standard ligation reactions were set up with up to 2 microgram of sized MboI DNA fragments and 400 nanogram of BamHI- digested, calf intestinal alkaline phosphatasetreated YEplac181 vector DNA. The vector YEplac181 is described in detail in an article by Gietz et al. (1988) entitled "New yeast-*Escherichia coli* shuttle vectors constructed with in vitro mutagenized yeast genes lackning six-base pair restriction sites" published in Gene, volume 74 on pages 537–544. Yeast transformation was carried out according to Schiestl et al. (1989) entitled "High efficiency transformation of intact yeast cells by single stranded nucleic acids as carrier" published in Current Genetics volume 16 on pages 339–346. This yeast transformation method is also described in detail in example 1.

As a measure of the efficiency of ligation, one microliter of each ligation library was transformed into the *Escherichia coli* strain DH5alpha. The presence of the lacZ fragment in YEplac181 allows the estimation of percentage of clones with inserts using the X-gal blue:white color screen described in the aforementioned Gietz et al. (1988) publication.

Ligation libraries were directly transformed into the yeast strain S35/2-10C and transformants were selected on medium lacking uracil. Strain RS35/2-10C is described in Schiestl et al. (1988) in a publication entitled "Analysis of the mechanism for reversion of a disrupted gene" published in Genetics volume 119 on pages 237–247 and has the genotype MATa; ura3-52; leu2-3,112; trp5-27; arg4-3; ade2-40; ilv1-92. Five URA3+ transformants were obtained, plamid DNA was isolated from these yeast colonies as described in example 1 and transformed into *E. coli*. as described in example 1. All of these five colonies contained DNA fragments of varying sizes but gave a 1.1 kilobasepair long frgment after digestion with HindIII. This fragment has been shown to contain the URA3 gene as described in the aforementioned paper by Gietz and Schiestl (1991).

One of these plasmids, plasmid pDB3 was used to determine the 5' and the 3' sequence outside of the 1.1 kilobasepair long URA3 fragment. Plasmid DNA was extracted from E. coli as described in example 1. The sequences flanking the URA3 insertions were determined using 18 bp primers homologous to the insertion 68 bp from the 5' (relative to URA3) junction 5' CGGAGATTACCGAATCAA (SEQ ID NO:1) and 42 bp from the 3' junction 5' GAATCTCGGTCG-TAATGA (SEQ ID NO:2).

Sequencing of double-stranded DNA was carried out with Sequenase[R] (product No. 70721) purchased from United States Biochemical Corp. of Cleveland, Ohio and was used according to the recommendation of the supplier. The DNA fragments were separated using a BioRad sequencing cell purchased from BioRad Laboratories of 2000 Alfred Nobel Drive, Hercules, Calif. and used according to the recommendations of the supplier. This sequence information was used to design the following primers for PCR amplification of the 5' and the 3' ends of the URA3 flanking sequence.

Plasmid pDB3 was used to amplify the 5' and the 3' end of the URA3 gene by the polymerase chain reaction including the rest of the plasmid. This PCR technology is very well described in U.S. Pat. Nos. 4,683,202, 4,683,195, 4,800,195 and 4,965,188. All products used for performing the PCR reaction have been purchased from Perkin Elmer Cetus Corporation of 761 Main Avenue, Norwalk, Conn. 06859. Oligonucleotides were synthesized with the DNA synthesizer Biosearch 8700 purchased from New Brunswick Company, Inc. of Edison, N.J. 08818 and operated with chemicals from Milligen/Biosearch, a division of Millipore of 186 Middlesex Turnpike, Burlington, Mass. 01803. All procedures were strictly followed as described by the aforementioned suppliers. A pair of oligonucleotides were synthesized with the following DNA sequence CGCGAATTC-CTTCACCATAAATATGCCTCG (SEQ ID NO:3 and ATATCCCGGGAACTATCCAATACCTCGGCA(SEQ ID NO:4). The oligonucleotides were after synthesis incubated for 6 hours in ammonium hydroxide at a temperature of 55 degrees Celsius (°C.) to remove the phosphoryl (cyanoethyl) protecting group. Thereafter the ammonium hydroxide was evaporated and the dry DNA pellet was dissolved in distilled water. These oligonucleotides were used to amplify with the aforementioned PCR technology the ura3-5' and the ura3-3' sequences and the amplified product was thereafter digested with EcoRI and SmaI, the EcoRI site was filled in with the Klenow fragment of DNA polymerase, and the ends were ligated. The resulting plasmid was amplified in *E. coli* and digested with BamHI, and yeast transformation was carried out as described above. Cells were plated onto complete medium and later replica plated onto medium containing 5 fluoroorotic acid. Thus, for example, an article by F. Winton et al. entitled "Eviction and Transplacement of Mutant Genes in Yeast" (Methods in Enzymology, 101:211–227 1983) discloses that a strain containing the URA3 gene cannot grow in medium containing 5-fluoroorotic acid. Thus only colonies deleted for the URA3 gene by the fragment containing only the ura3-5' and the ura3-3' sequences was selected for.

By way of illustration and without limitation, one can delete the URA3 gene by using the aforementioned plasmid containing the ura3-5' and the ura3-3' sequences and cloning a TRP1gene into this plasmid next to the ura3 sequences. One can then select for integration of the plasmid on medium lacking tryptophan and later select for deletion of the URA3 gene on medium containing 5 fluoroorotic acid as mentioned above.

By way of further illustration, the URA3 gene may be replaced by LYS2. When a strain containing the LYS2 allele is present, then the strain is unable to grow in a medium containing alpha-aminoadipic acid. But the deletion strain constructed by ways known to those skilled in the art can grow in the presence of alpha-aminoadipic acid. See, e.g., an article by Barnes and Thorner entitled "Use of the LYS2 Gene for Gene Disruption, Gene Replacement, and Promoter Analysis in *Saccharomyces cerevisiae*, "Gene Manipulations in Fungi," (Academic Press, Inc., 1985) .Those in the art are aware of the identity of those media which select against various genes. Thus, for example, an article by J. R. Broach et al. entitled "Development of a hybrid cloning vector and isolation of the CAN1 gene", (Gene 8:121–133, 1979) discloses that a strain containing the CAN1 gene cannot grow in the presence of cana vanine; the article also describes the CAN1 gene.

In one preferred embodiment of applicant's process, the yeast cells used lack extended sequence identity to the transforming plasmid or fragment used in the process. In this aspect of applicant's process, an artificial deletion of the yeast is not necessarily required to produce the starting material. Thus, one may utilize yeast cells which have been subjected to a naturally-occurring deletion. Alternatively, or additionally, one may seek to incorporate into the yeast cells a gene from a heterologous source such as, e.g., a gene from another organism. Thus, one may incorporate a bacterial gene into the yeast cell. Thus, one may incorporate an animal gene into the yeast cells.

To determine whether one certain fragment of DNA is useful in applicant's process, one may carry out a Southern blot at very low stringency to determine that no extended sequence identity exists, that is when no specific hybridization is detectable, the fragment is useful. Methods for Southern bloting are well known to those skilled in the art and can be found e.g. in a book entitled "Molecular Cloning: a Laboratory Manual", second edition, by Sambrook et al on pages 9.31 to 9.59 published by Cold Spring Harbor Laboratory Press, Cold spring Harbor, N.Y. Southern bloting is also described in a later part of this specification and may for the present purpose be carried out with hybridization conditions using 0.50% formamide, one molar sodium chloride at 42 degrees celsius and with two washes for 15 minutes containing 2 times SSC and 1 percent SDS at room temperature.

By way of illustration and without limitation, genes other than URA3 can be used for illegitimate integration such as the LEU2, TRP1, LYS2, ADE2, HIS3 or the like. In case these genes are used, the corresponding homologous chromosomal sequences should be deleted by ways suitable for these alleles known to those skilled in the art.

In one embodiment of applicant's process, the abovementioned strain RSY12 is used for transformation with construct 10 according to protocols known to those skilled in the art. This embodiment is also described in a publication by applicant and Thomas D. Petes entitled "Integration of DNA fragments by illegitimate recombination in *Saccharomyces cerevisiae*", published in Proceedings of the National Academy of Science, U.S.A., Volume 88, pages 7585–7589, September, 1991.

In the first step of this embodiment of applicant's process, a viable strain of yeast cells is provided. In one preferred embodiment, the yeast cells are from the species *Saccharomyces cerevisiae*. This species has been described in U.S. Pat. No. 4,997,757. It will be apparent to those skilled in the art, however, that other yeast species also may be used with the process.

The gene which is to be incorporated, and which preferably is nonhomologous, may be in the form of a DNA fragment. Alternatively, the gene may be incorporated into a plasmid.

The DNA fragment may be cut from a plasmid by restriction enzyme digestion; this digestion process is well known to those skilled in the art and is described elsewhere in this specification in the definition of the term "restriction enzyme." The DNA fragment will be cut at the site specific for the particular restriction enzyme used.

Referring to FIG. 1, it will be seen that gene fragment 10 is a 1.1 kilobase pair long gene fragment containing the entire URA3 gene 12. The gene fragment 10 illustrated in FIG. 1 is a cleavage product which was cleaved with restriction enzyme BamHI.

The BamHI restriction enzyme is commercially available and may be obtained, e.g., from the Fisher Scientific Company. Thus, for example, pages 4–16 of Fisher-Scientific Bulletin No. 653C U.S., entitled "Biotechnology Source 87/88," describes the properties and uses of restriction enzymes in detail. The BamHI enzyme is described on page 5 of the catalog, and it is indicated that it recognizes the 5' . . . G/GATCC . . . 3' site.

It will be apparent to those skilled in the art that the restriction enzyme(s) used in applicant's process will depend upon the sites in the yeast genes where cutting is to occur. Because of the wide variety of commercially available restriction enzymes, applicant's process affords a substantial degree of flexibility. Furthermore, as is known to those in the art, many other restriction enzymes are also available from researchers on a non-commercial basis. The procedure for digesting plasmids with restriction enzymes and of isolating the fragments so digested is well known to those skilled in the art. Thus, by way of illustration and not limitation, one may refer to a publication by T. Maniatis et al. entitled "Molecular Cloning: A Laboratory Manual", (Cold Spring Harbor Laboratory, Cold Spring Harbor, N.Y., 1982). In the Maniatis Laboratory Manual, restriction enzymes are disclosed on pages 97–107, and the isolation of gene fragments by Gel Electrophoresis, if needed, is described on pages 149–186. Thus, for instance, it may be required to isolate a specific construct 10 from a mixture of fragments after digestion of a plasmid, if one of these fragments shows extensive homology to the genomic DNA.

Chromosomal DNA is a double-stranded DNA. When it is contacted with the BamHI restriction enzyme, it is recognized at the DNA sequences where the GGATCC base sequences appear. When chromosomal DNA is contacted with both the BamHI restriction enzyme and URA3 fragment 10, the URA3 fragment 10 is integrated into restriction recognition sites in the genomic DNA to produce a modified yeast chromosomal DNA. Because the 5' overhanging ends of fragment 10 are compatible with the 5' overhanging end of restriction recognition site, the compatible base sequences hybridize with each other.

In one embodiment of applicant's process, DNA fragment 10 is first provided by digestion of plasmid with the BamHI restriction enzyme. Thereafter, using the one of the transformation processes described above, in one embodiment the DNA fragment 10 is incubated together with the restriction enzyme. Other enzymes may also be used in applicants process as long as they are working in a similar manner to the one shown in applicant's process for BamHI which is to catalyze integration events into chromosomal DNA. In another embodiment the DNA fragment 10 in the absence of the restriction enzyme is used to transform the yeast strain.

To obtain portions of construct 10 in the presence of the restriction enzyme as well as portions of construct 10 in the absence of the restriction enzyme the digested plasmid DNA pM20 comprised of DNA fragment 10 and vector DNA can be precipitated with ethanol, and resuspended in 200 microliter of 0.01M Tris-HCl (pH7.5), 0.05M EDTA, 1 percent (%) SDS, and 100 microgram per milliliter of proteinase K. After a 30 minutes incubation at 37 degrees centigrade, the sample can be extracted twice with phenol:chloroform:isoamyl alcohol, precipitated with ethanol, washed with 70% ethanol, and vacuum-dried. The pellet can be dissolved in water. Thereafter, the sample is divided into two aliquots and to one aliquot 100 units of the respective restriction enzyme is added and this mix is transformed into the cells using the yeast transformation method described below. In the present example BamHI is used.

By way of illustration and not limitation, one can use the "High efficiency transformation method of intact yeast cells using single stranded nucleic acids as carrier" disclosed by R. Schiestl and D. Gietz in an article published in Current Genetics 1989 volume 16 on pages 339 to 346 or any further development thereof such as the one published by Gietz and Schiestl 1991 in Yeast volume 7 on pages 253 to 263 or another method of transformation by electroporation published by Becker and Guarente 1991 in Methods in Enzymology, volume 194 on pages 182 to 186. 300 milliliters of a culture of strain RSY12 in YEPD medium was grown overnight to 5 to $7 \times 10^6$ cells per milliliter from a fresh overnight culture. Cells were collected by centrifugation at 5,000 rounds per minute (rpm) for 5 minutes in a GSA rotor in a Sorvall centrifuge. The cells were resuspended in 1.5 milliliters of a solution of Tris/EDTA, pH 7.5 (hereinafter called TE) and 0.1 molar lithium acetate (obtained from Sigma Chemical Company of St. Louis, Mo. 63178) and incubated under shaking at 30 degrees Celsius for one hour. Five micrograms of the digested plasmid PM20 min the presence of 100 units of the respective restriction enzyme (for restriction enzyme mediated integration events) or in the absence of any added restriction enzyme (for illegitimate integration events) were mixed with 200 micrograms of sonicated salmon sperm carrier DNA. 20 microliters of a solution of denatured salmon sperm DNA (10 milligrams per milliliter (mg/ml)), obtained from Sigma Chemical Company, dissolved in TE buffer, sonicated with a MSE 150 Watt Ultrasonic Disintegrator (obtained from Measuring and Scientific Equipment Ltd. Manor Royal, Crawley, Great Britain) for 10 minutes, extracted once with an equal volume of phenol, precipitated with twice the volume ethanol, dried under vacuum produced by a water pump and redissolved in TE buffer in an Eppendorff tube and 0.2 milliliter of the cell suspension was added to the DNA. The suspension was incubated for 30 minutes at 30° C. with agitation in a New Brunswick controlled environment shaker. Thereafter 1.2 milliliters of a solution containing 40% polyethylene glycol 4000 (obtained from Sigma Chemical Company), TE buffer with a pH of 7.5 and 0.1 molar lithium acetate was added and the solution was gently mixed. The solution was incubated for another 30 minutes at 30 degrees centigrade with agitation and thereafter heated for 7 minutes in a 42 degrees centigrade waterbath. The cells were then collected by centrifugation in a Fisher microfuge for 5 seconds, washed twice with TE buffer with a pH of 7.5 and finally resuspended in one milliliter of TE buffer. 0.2 milliliters of this cell suspension was plated onto one petridish containing medium lacking uracil.

Regardless of what method of transformation is used, the transformants (integrants, genome rearrangement) should be identifiable. As those skilled in the art are aware, one can measure the rate of URA+ colonies by conventional means. Thus, for example, one can plate certain numbers of cells on a medium lacking uracil. This and other yeast genetics methods are described in detail in a publication by F. Sherman et al. entitled "Methods in yeast genetics, a laboratory manual" (Cold Spring Harbor Laboratory, Cold Spring Harbor, N.Y., 1986).

A suitable medium for permitting growth of the cells which did not undergo genome rearrangement is "YEPD". This medium contains yeast extract (one percent, by weight), peptone (any of various protein compounds obtained by acid or enzyme hydrolysis of natural protein, which is present in a concentration of 2 percent, by weight), dextrose (2.0 percent by weight), agar (2 percent by weight), and water. For each and every one of the constructs described in FIGS. 1–5, this medium permits the growth of all cells. Other such media known to those skilled in the art also may be used for this purpose such as, e.g., "synthetic complete medium".

Synthetic complete medium contains yeast nitrogen base without amino acids and with ammonium sulfate, (0.67 percent, by weight, which can be purchased from Difco Laboratories of Detroit, Mich.), dextrose (2 weight percent), agar (2 weight percent), water, and the following amino acids and bases per liter of total solution: 20 milligrams each of L-trypthophan, L-histidine hydrochloride, L-arginine hydrochloride, L-methionine, L-isoleucine, L-tyrosine, L-lysine hydrochloride, adenine sulfate, and uracil; 30 milligrams per liter of total solution of L-leucine; 350 milligrams of L-threonine per liter of solution; and 75 milligrams per liter of Lvaline. It is recommended that the use of the aforementioned selective system or similar systems within the scope of this invention may include incubation in medium containing galactose instead of glucose before, during or after exposure of the cells to the agents to be tested.

Other suitable growth media can also be used. Thus omissions, and/or additions may be made in the concentrations and/or the compositions of the media described above without adversely affecting their performance.

Insertion of the URA3 gene or the like by illegitimate recombination gives rise to a variety of colonies with different insertions. These represent a pool of different mutants which can be screened for the desired phenotype, like radiation sensitivity, auxotrophy or the like. Insertional mutagenesis has the advantage that the point of insertion can be easily mapped by following the segregation of the prototrophic marker URA+ in case of construct 10 and the sequences at the insertion points can easily be cloned, as described in the aforementioned Schiestl and Petes paper and in the examples.

In another preferred embodiment the frequency of identifiably URA+ colonies is exactly measured. One of the advantages of applicant's process is that this frequency is substantially increased in the presence of carcinogens.

As used in this specification, the term "identifiable" refers to a rearrangement (insertion in case of construct 10) which, when the cells in which it is present are growing in a suitable selection medium, cause the cells to exhibit some phenotype which is different from that of cells which have not undergone rearrangement. Thus, by way of illustration, if the genome rearrangement causes the cells to form countable and/or visible colonies, the rearrangement is identifiable if cells which have not undergone the rearrangement do not form countable and/or visible colonies in the selection medium. Thus, by way of illustration, if the genome rearrangement causes the cells to form colonies identifiable by different color from the colonies which have not undergone the rearrangement, the rearrangement is identifiable. Thus, by way of illustration and not limitation, if the genome rearrangement causes the cells to grow, the growth of these cells in selection medium can be measured by the technique described in U.S. Pat. No. 4,256,832 of Findl et al. (which technique detects oxygen consumption of growing cultures), and this growth is thus identifiable.

Another preferred embodiment of this invention is the use for restriction enzyme mediated recombination of the technology of Szybalski entitled "Universal restriction endonuclease" published in U.S. Pat. No. 4,935,357. This process utilizes a restriction enzyme that cuts at a site away from its recognition site. An oligonucleotide is made that contains a palindrome to folds and anneals to create the recognition site for said restriction enzyme. Used in our process the double stranded portion of this oligonucleotide would be ligated to the URA3 fragement or any other fragment. The single stranded portion of the oligonucleotide is designed so that it is homologous to a specific target site in the genome of the organism. The fragment together with the restriction enzyme are transformed into the cells. The next step is that the single stranded portion of the oligonucleotide finds its homologous chromosomal position and anneals with the chromosomal DNA. This step can be facilitated by the addition of single strand binding proteins and/or RecA protein or the like. This annealing reaction to the chromosomal homologous DNA position creates double stranded DNA that is now a substrate for the restriction endonuclease to cut. This creates at least a nick at the target site which increases the frequency of recombination into that genomic sequence by restriction enzyme mediated recombination or by illegitimate recombination. The tremendous advantage of this embodiment lies in the fact that depending on the choice of the single stranded portion of the oligonucleotide one can direct the enzyme to specific positions in the genome and thus can create specific nicks within the genomic DNA that serve as substrates to increase the frequency of integration into these sequences.

Figure 3:
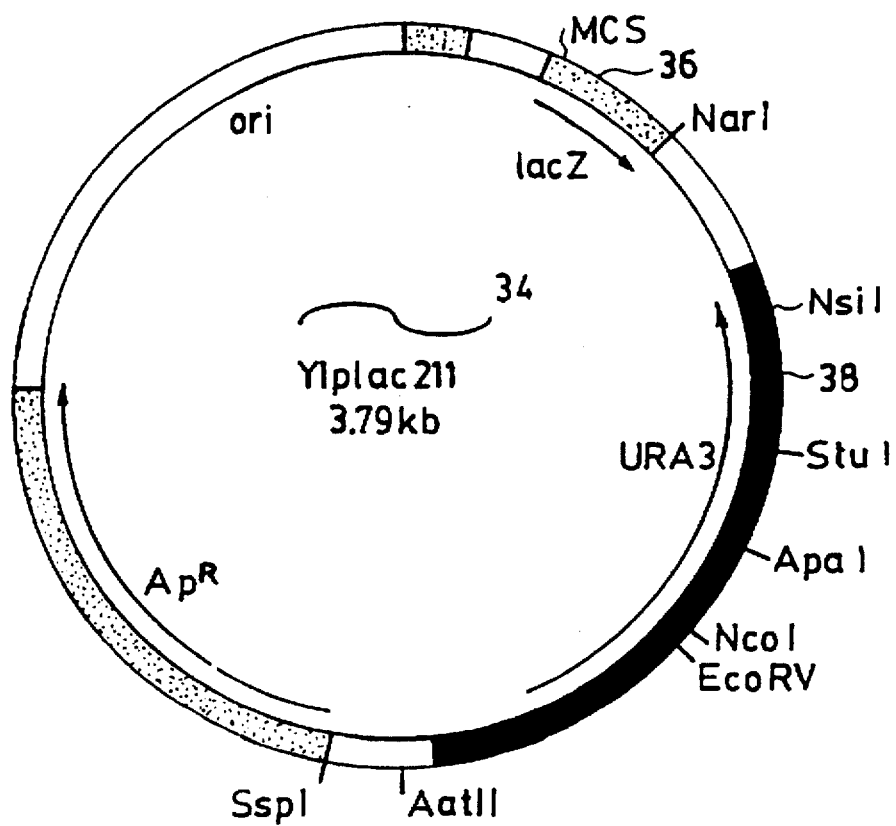
FIG. 3 is a schematic of another preferred embodiment, plasmid YIplac211, containing a functional URA3 allele, which can be used as recombination substrate instead of the URA3 fragment shown in FIG. 1.

FIG. 3 illustrates plasmid YIplac211 (construct 34) which is used as a recombination substrate in one of applicant's preferred embodiments instead of construct 10 of FIG. 1. The construction and use of plasmid YIplac211 is very well documented in a publication by D. Gietz et al. 1988 published in Gene 74 on pages 527 to 534. Construct 34, contains the URA3 gene 38 in its backbone and is useful in the same manner as described above for construct 10. All plasmids of the YIp series published in the aforementioned Gietz et al. paper are useful in applicants process as long as the specific yeast genes contained on those plasmids have been mostly deleted from the genome of the respective yeast strains. Plasmid YIplac211 as well as the other useful plasmids published in the aforementioned paper by Gietz et al. are freely available to those skilled in the art from Dan Gietz at the aforementioned address. Plasmid YIplac211 is digested with BamHI and used for transformation of strain RSY12 as mentioned above for construct 10. There is a unique BamHI site in construct 34 within the multi cloning site at region 36. By way of illustration and not limitation all restriction enzymes that digest plasmid YIplac211 are useful in applicants process. In addition all plasmids or DNA fragments are useful in applicant's process as long as they do not show any extended homology to the genomic DNA of the species of yeast used in applicant's process.

Figure 4:
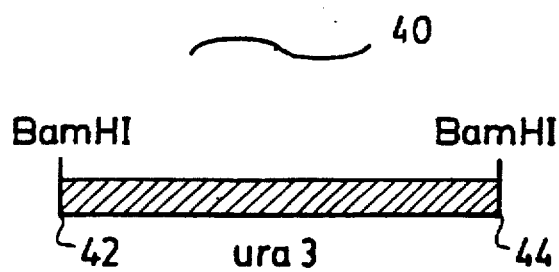
FIG. 4 is a schematic of the constituents of yet another preferred embodiment, the promoterless, nonfunctional ura3 fragment, which can be used as recombination substrate instead of the URA3 fragment shown in FIG. 1.

FIG. 4 illustrates a nonfunctional internal ura3 fragment 40 which is flanked by BamHI sites 42 and 44. This ura3 fragment is another preferred embodiment which can be used in applicant's process. This fragment has been constructed by Dan Gietz and is similar to the one described by Alani and Kleckner 1987, Genetics 117 on pages 5 to 12. In the same disclosure it has been shown that the nonfunctional promotorless ura3 fragment can be integrated in frame within the open reading frame of several other genes and that it can produce functional URA3 gene product. This ura3 fragment is useful in applicant's process when the URA3 genomic copy is deleted to integrate by illegitimate recombination into the genome. URA3+ colonies will only arise if integration occurs in frame within the open reading frame of an expressed gene.

For applicant's process a similar construct has been developed. To construct the nonfunctional ura3 allele the polymerase chain reaction is used as described above. A pair of oligonucleotides were synthesized with the following DNA sequences: CGCGGATCCTATAAGGAACGTGCTGCTACTCAT (SEQ ID NO:5) and CGCGGATCCCGGGTAATAACTGATATAA (SEQ ID NO:6). These oligonucleotides were used to amplify with the aforementioned PCR technology the promotorless ura3 fragment from plasmid YEp24, which is readily available to those skilled in the art and has been described in the aforementioned publication by Botstein et al. 1979. The amplified ura3 fragment was digested with BamHI and ligated into the BamHI site of pUC19. The resulting plasmid, termed pRDG369, was amplified in *E. coli* by means known to those skilled in the art and was used to select for illegitimate integration events into expressed genes. For this purpose plasmid pRDG369 was digested with the restriction enzyme BamHI and yeast transformation was carried out with the aforementioned method. As described in example 3, we did obtain several URA3+ colonies that proved to be the result of in frame integration events into the open reading frame of expressed genomic genes.

Figure 5:
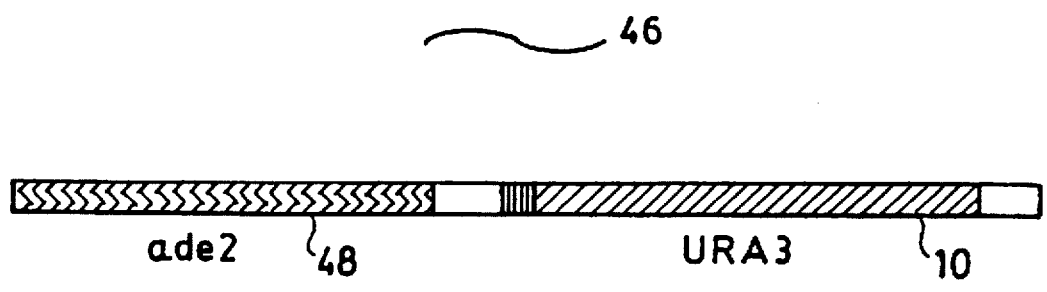
FIG. 5 is a schematic of the constituents of yet another preferred embodiment showing the promoterless, nonfunctional ade2 gene together with the functional URA3 fragment.

FIG. 5 illustrates construct 46, another preferred embodiment within the scope of this invention. Construct 46 comprises the aforementioned construct 10, the functional URA3 gene as shown in FIG. 1 and construct 48 which is a nonfunctional, promotorless ade2 gene. The structure and DNA sequence of the ADE2 gene has been published by A. Stolz and P. Linder, 1990 in Gene volume 95 on pages 91 to 98. The ADE2 gene is freely available to those skilled in the art from several sources including the authors of aforementioned publication at the Department of Microbiology, Biocenter, CH-4056 Basel, WO 93/23534 PC Ir/US93/04847 Switzerland. To use construct 46 in applicants process the genomic ADE2 gene would have to be deleted to remove most of the homology according to the process described above for the URA3 gene or according to the process described in the aforementioned publication by Stolz and Linder. In addition, the URA3 gene would have to be deleted as mentioned above. Since the sequence is published it is easy to construct the nonfunctional promotorless ade2 gene just like in the aforementioned case with the nonfunctional ura3 gene construct 40. One significant advantage to use the ADE2 gene is the fact that ade2 mutants are red on medium with limited adenine of around 5 milligram adenine per liter of medium, whereas strains with a functional ADE2 gene are white on such medium. This change in color simplifies the screen for adenine expression since the colonies only have to be tested for their color. In addition, it may be possible to differentiate slight color changes as different degrees of pink between white and red.

Construct 46 will be used in the same way as construct 40 but has the advantage that the URA3 gene can be used for selection of any integration event independent of the requirement to integrate into an expressed gene in frame. However, the advantage of construct 40 is that the promotorless ade2 gene can be used as a reporter gene to determine the fraction of events integrated into expressed genes, but even more important to construct a random library of integration events which thereafter can be assayed for various inducing conditions. Thus, for instance, if construct 40 would have integrated in frame into a heat shock gene the ade2 gene would only be expressed after heat shock, thus, for instance if construct 40 would have integrated into DNA damage inducible gene the ade2 gene would only be expressed in the presence of DNA damage. Whatever the inducing conditions would be they may be applied and the library could be screened for ade2 expression under these conditions. Thereafter, the disrupted genes may be cloned in ways described above.

This construct may or may not contain any sequence between constructs 10 and 48. For the purpose of illustration and without limitation, this sequence may be the pUC19 sequence which would greatly simplify retrieving the integrated plasmid from the genome.

Another use of construct 46 within the scope of this invention to use the strain after integration into the genome when the strain is still ade−. Selection can be applied for ADE+ colonies. These ADE+ colonies can arise by a further genome rearrangement. Strains with construct 46 integrated into their genome can thus be used to select for a further genome rearrangement leading to ADE+ which can be used to screen for mutants showing a lower or a higher frequency of illegitimate recombination. It can also be used to test for the effect of carcinogens on this process as described later.

In yet another preferred embodiment of applicant's process, cells of the slime mold Dictyostelium discoideum are used in conjunction with a specified medium to select for restriction enzyme mediated recombination events. The slime mold used in this process must undergo illegitimate recombination or restriction enzyme mediated recombination events between DNA sequences without extended DNA sequence homology and thus cause genome rearrangement which must be selectable or otherwise identifiable.

The slime mold Dictyostelium discoideum is a model system for developmental genetics because for part of its life cycle it is a unicellular amoebae and as such it is very well amenable to molecular biology approaches. After aggregation, however it forms multicellular fruiting bodies. Many of the genes for aggregation and fruiting body formation are dispensable in its life stage as unicellular amoebae such that mutants deficient in these processes can be obtained and studied, see e.g a book by W. Loomis entitled "Dictyostelium discoideum: a developmental system" published by Academic Press, New York, 1975. In addition, like the aforementioned yeast, Dictyostelium shows a relatively high frequency of homologous recombination, which allows one to readily make specific constructions in the genome. Thus, for example, one can readily reintroduce certain in vitro constructed altered genes into its genomic position. Because of its properties, Dictyostelium is extremely useful for developmental biology.

However, one of the most important problems with the development of Dictyostelium as research tool is that cloning by functional complementation with plasmid-borne genomic libraries has not been successful for developmental genes where direct selection cannot be applied. A method for insertional mutagenesis would be a breakthrough for developmental biology with Dictyostelium and many other organisms.

Not every species of said slime mold works in the process of this invention. The process utilizes those viable species of Dictyostelium which can be transformed with DNA or which contain a DNA fragment on a plasmid or integrated into the genome which is selectable for after addition and/or intracellular expression of (a) restriction enzyme(s). Thus, by way of illustration, such species of Dictyostelium may contain a mutation in the pyr5-6 gene. Thus, by way of illustration, Dictyostelium chromosomes normally contain one pyr5-6 gene. In order to be used for one preferred embodiment in the process of this invention, the Dictyostelium chromosomes should contain a mutation or should be mutated in the pyr5-6 gene or any other gene that can be used for transformation. In one preferred embodiment the pyr5-6 gene is deleted for its entire open reading frame removing most of the homology to the integrating fragment so that homologous recombination does not occur at a frequency interfering with selection for illegitimate recombination or restriction enzyme mediated recombination events which are the objects of this specification.

By way of illustration and not limitation, the transforming DNA used in conjunction with said process, may contain functional elements, such as the entire pyr5-6 gene or the like.

In another preferred embodiment, the transforming DNA used in conjunction with said process, may contain nonfunctional elements, such as fragments of the pyr5-6 gene or the like, that lack their own promoter and/or the first several amino acids of the gene product. In this preferred embodiment, the promoterless gene is rendered functional only after restriction enzyme mediated recombination or illegitimate recombination with the genome of said Dictyostelium strain such that the transforming DNA fragment acquires a functional promoter from the genomic DNA of said strain. Therefore, the functional pyr5-6 gene or the like is the result of restriction enzyme mediated or illegitimate recombination events leading to integration of the promoterless fragment into the genome of said strain. To be used to select for illegitimate recombination, a deletion of the pyr5-6 gene may be constructed as described below to remove most of the homology to the genome so that homologous recombination does not interfere with the selection.

In another preferred embodiment of said process functional or nonfunctional elements may be used in conjunction with restriction enzymes as long as they they are selectable for either self sufficient (functional elements) or after integration into the genome by illegitimate recombination or by restriction enzyme mediated recombination, whereby they may acquire a promoter as described above (nonfunctional elements). By way of illustration and not limitation for this purpose the bacterial neomycin gene can be used which confers resistance to G418 in Dictyostelium see e.g a publication by Knecht et al. entitled "Developmental regulation of Dictyostelium discoideum actin gene fusions carried on low-copy and high-copy transformation vectors" published in Molecular and Cellular Biology 6:3973–3983. In comparison the the normal Dictyostelium cells are sensitive to G418. By way of illustration and not limitation other genes conferring resistance to different drugs or which are otherwise selectable for may be used.

Figure 6:
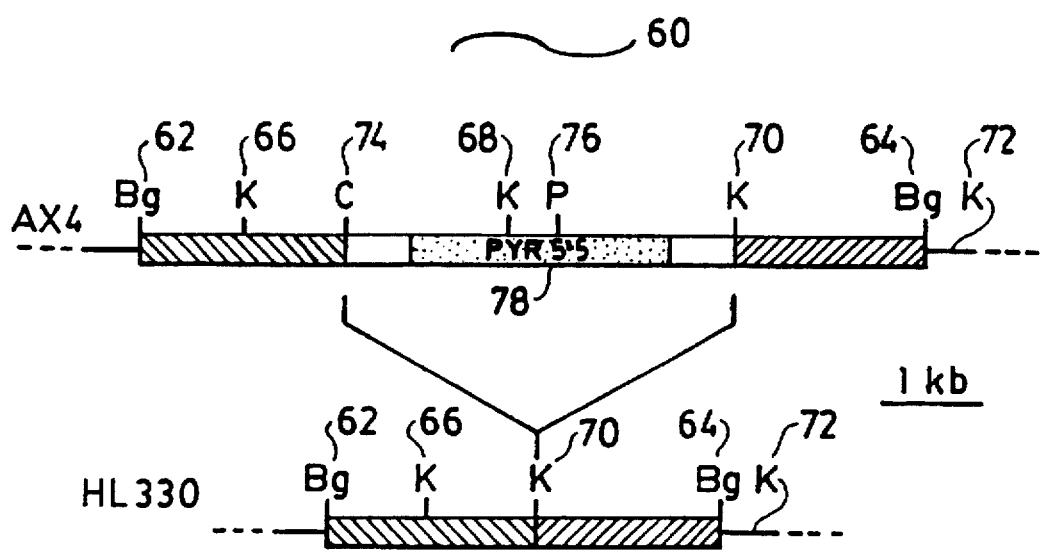
FIG. 6 is a schematic of the pyr5-6 locus of the wildtype Dictyostelium discoideum strain and of one possible pyr5-6 deletion mutant used in applicant's process shown in FIG. 7.

FIG. 6 illustrates construct 60, which is a schematic of the wildtype PYR5-6 region in chromosomal DNA of wildtype strain AX4 of Dictyostelium discoideum. Strain AX4 is a clonal isolate of strain AX3, is described in the aforementioned publication by Knecht et al., is widely used and is available from William Loomis at the Department of Biology, University of California, San Diego, La Jolla, Calif. 92093. Strain AX3 is even more widely used and is described in a publication by W. Loomis published in Experimental Cell Research 64:484–486 (1971). Referring again to FIG. 6, the following restriction sites in the PYR5-6 region are shown. BglII sites at points 62 and 64, KpnI sites at points 66, 68, 70 and 72, a ClaI site at point 74, a PvuII site at point 76. As can be seen, there is a KpnI site at point 68 and the PvuII site at point 76 within the PYR5-6 gene 78. Strain HL330 was deleted for the PYR5-6 gene between points 74 and 70 to give rise to the deletion allele 80. Strain HL330, was used for studies on restriction enzyme mediated recombination.

To construct strain HL330 strain AX4 was used. Strain AX4 was grown on HL-5 medium containing (per liter) 10 gram of glucose, 5 gram of BBL yeast extract which can be purchased by Fisher Scientific Co. of 711 Forbes Ave., Pittsburgh, Pa. 15219. 5 grams of Thiotone produced by the aforementioned BBL, 5 grams of Proteose peptone from Difco also obtainable through Fisher Scientific Co., 0.34 grams of $KH_2PO_4$ and 0.67 grams of $Na_2HPO_4$. $7H_2O$ and 50 milligram of dihydrostreptomycin sulfate. The medium was sterilized by autoclaving for 20 minutes at 121° C.

A 6.7 kilobase pair long DNA fragment which includes the pyr5-6 gene was subcloned from a yeast artificial chromosome clone 188. Intact YAC188 was separated from the endogenous yeast chromosome as described in a publication by Kuspa et al. published in Genomics 13 on pages 49 to 61, 1992. The YAC188 chromosome was isolated as a gel slice, and digested in situ with BglII. The YAC188 BglII fragment was then electroeluted onto DE81 paper. This was done in the following way. A gel was prepared with agarose as described previously. The DNA was made visible under UV light by staining with 0.5 micrograms per milliliter ethidium bromide and the desired band was located. The DNA fragment was isolated according to a publication by Dretzten et al. entitled "A reliable method for the recovery of DNA fragments from agarose and acrylamide gels" as appeared in Analytical Biochemistry 112 on pages 295 to 298 (1981). An incision was made with a scalpel in front of the band and a piece of Wattman DE81 DEAE-cellulose paper (obtained from Fisher Scientific of Pittsburgh, Pa) was inserted. The band was allowed to enter the DEAE paper by further electrophoresis in the same direction and thereafter the paper was removed from the gel. The paper was placed into a 0.4 ml Eppendorff tube and a hole was made in the bottom of the tube, the tube was placed inside a 1.5 ml Eppendorff tube and spun for 15 seconds in a Fisher microfuge, 0.1 ml of elution buffer containing 1 molar sodium chloride was added and the elution buffer collected by centrifugation. This was repeated twice and the eluate was extracted once with an equal volume of phenol, once with a 1:1 mix of phenol chloroform and once with chloroform. The solution obtained was precipitated with twice the volume of ice cold ethanol for 30 minutes at −20° C. Thereafter, the precipitate was washed with a 70% solution of ethanol, vacuum dried, and redissolved in 10 ml of double distilled water. This DNA fragment was cloned into the BamHI site of the plasmid pGEM3 which was obtained from Promega Corporation (which can be purchased through the aforementioned Fisher Scientific Co) using standard cloning techniques as described above and in the above mentioned Maniatis et al. book. Plasmid p188.50 was identified from this sublibrary by colony blot hybridization with a $^{32}$P-labeled pyr5-6 gene probe isolated from the plasmid pDU3B1 which is described in a publication Boy-Marcotte et al. entitled "A DNA sequence from *Dictyostelium discoideum* complements ura3 and ura5 mutations of *Saccharomyces cerevisiae*" published in Molecular and General Genetics 193 on pages 406 to 413. This was done to confirm by Southern blot analysis that the plasmid p188.50 contains a 6.7 kilobase pair long fragment surrounding the gene with a restriction map that matched the map obtained from the AX4 genome of FIG. 6. The plasmid pPYR is analogous to p188.50 except that the central 3.3 kilobase pair long fragment between the restriction sites ClaI point 74 of FIG. 6 and KpnI, point 70 of FIG. 6 is missing. pPYR was constructed by ligating the 1.7 kilobase pair long HindIII-ClaI fragment (upstream of pyr5-6) of p188.50 into HindIII/AccI digested aforementioned plasmid pGEM3 and then ligating the 1.7 kilobase pair long KpnI fragment (downstream of pyr5-6) of p188.50 into this vector's KpnI site. A 3.4 kilobase pair long HindIII-EcoRI fragment was purified from pPYR and used to transform AX4 to 5-fluoroorotic acid (5-FOA) resistance. Analogous to the aforementioned situation in yeast 5-FOA selects against the pyr5-6 function as described in a publication by D. Kalpaxis et al. published in Molecular and General Genetics 225 on pages 492 to 500, 1991.

Transformation of strain AX4 was carried out by a modification of the procedure by Howard et al. entitled "Establishment of a transient expression system for *Dictyostelium discoideum*" published in Nucleic Acids Research 16 on pages 2613 to 2623. Strain AX4 was grown to $1–2\times10^6$ cells per milliliter of the aforementioned HL-5 medium or HL-5 supplemented with 20 to 200 microgram per milliliter of uracil. The cells were then pelleted in a conical 50 ml tissue culture tube at 1000 rounds per minute in a clinical centrifuge. The media was decanted and as much residual media as possible was aspirated from the walls of the tube prior to resuspending the cells in ice-cold electroporation buffer to a concentration of $10^7$ cells per milliliter. At this point, cells, glass tube, and cuvettes were kept on ice. Plasmid DNA was used either undigested or linearized with a particular restriction enzyme and purified by phenol extraction and ethanol precipitation as described above prior to using it for transformation. Aliquots (0.8 milliliters) of the cell suspension were mixed with 40 microgram of DNA in a glass test tube and immediately exposed to 2.25 kilovolts per centimeter in a 0.4 centimeter gap electroporation cuvette in a BioRad gene pulser (obtained from BioRad of 85A Marcus Drive, Melville, N.Y. 11747) set at 0.9 kilovolts and 3 microfarad. Time constants ranged from 0.6 to 1.1 milliseconds. Otherwise the BioRad gene pulser was operated as recommended by the supplier. The pyr 5-6 deletion strain HL330 was isolated by screening the Dictyostelium transformants by Southern blot analysis for the absence of the central 2.0 kilobase pair long KpnI fragment of p188.50.

Referring now to FIG. 7, strain HL330 was used for restriction enzyme mediated integration events of construct 90, plasmid DIV2 into the genome. Construct 90 contains the pyr5-6 gene for selection in the host HL330, the amp$^r$ gene 94 and an origin of replication 96 both for amplification in *Escherichia coli*. Construct 90 can be digested with the restriction enzyme BamHI at a single site 98. For transformation of construct 90 into the cells, 100 to 200 units of restriction enzyme were mixed with the cell/DNA mixture and electroporation was carried out as described above. For use of the Sau3A enzyme BamHI digested vector DNA was used. Restriction enzymes were obtained from Life Technologies, Inc. of 8400 Helgerman Court, Gaithersburg, Md. 20877. Cells were plated in standard petri dishes immediately following electroporation at $1–2\times10^5$ cells per milliliter in FM medium (as defined below) or in the aforementioned HL-5 medium containing 100 micrograms per milliliter of the aforementioned 5-FOA and 20 microgram per milliliter of uracil and incubated at room temperature. FM medium is described in a publication by Franke et al. entitled "A defined minimal medium for axenic strains of *Dictyostelium discoideum*" published in the Proceedings of the National Academy of Sciences of the USA 74 on pages 2157 to 2161. FM medium contained the following substances: in millimol (mM) 56 mM glucose, Amino acids: 3.3 mM L-arginine, 2.3 mM L-asparagine, 1.7 mmM L-cysteine, 12.0 mM glycine, 3.4 mM L-glutamic acid, 1.4 mM L-histidine, 4.6 mM L-isoleucine, 6.9 mM L-leucine, 4.9 mM L-lysine, 2.0 mM L-methionine, 3.0 mM L-phenylalanine, 7.0 mM L-proline, 4.2 mM L- threonine, 1.0 mM L-tryptophane, 6.0 mM L-valine, vitamins in milligram per liter (mg/l) 0.02 mg/l biotin, 0.005 mg/l cyanocobalamin, 0.2 mg/l folic acid, 0.4 mg/l lipoic acid, 0.5 mg/l riboflavin, 0.6 mg/l thiamine. HCl, salts in millimol (mM) 5 mM $K_2HPO_4$, 2.0 mM NaOH, 0.2 mM $NaHCO_3$, 1.0 mM $NH_4Cl$, 0.02 mM $CaCl_2$, 0.10 mM $FeCl_3$, 0.4 mM $MgCl_2$, trace elements in micromol: $Na_2EDTA$, 1.8 M $H_3BO_3$, 0.7 moles $CoCl_2$, 0.6 moles $CuSO_4$, 0.08 m $(NH_4)_6Mo_7O_{24}$, 2.6 M $MnCl_2$, 8 M $ZnSO_4$, and 50 milligram per liter of dihydrostreptomycin sulfate. Transformation frequencies ranged from $5 \times 10^{-6}$ to $8 \times 10^{-5}$. For FOA selection, the medium was changed every 4–6 days and clones appeared in 2–3 weeks, after which the transformants were cloned by replica plating them in association with *K. aerogenes* on SM plates as described by M Sussman published in Methods in Cell Biology 28 on pages 9 to 29, 1987. For uracil prototrophic selection in FM medium, the FM was changed after 6–8 days and transformants were cloned on SM plates after 12 to 14 days. Referring again to FIG. 7, when host strain HL330 was transformed with construct 90 a frequency of transformation of about $5 \times 10^{-7}$ was obtained. When transformation of strain HL330 was carried out after construct 90 was digested with the BamHI or the EcoRI enzyme in the presence of the same enzyme it appears that a 20 to 60 fold higher frequency of transformation was obtained than in the absence of said enzyme. As a control, heat denatured BamHI was used and no stimulation of the rate of transformation was found. This proves that active restriction enzyme is required to stimulate the frequency of integration of linear DNA into Dictyostelium cells.

Evidence that the plasmid integrated into the host HL330 at one of its restriction sites 100 would be the clean excision of the 6.7 kilobase pairs long construct 90 upon digestion of genomic DNA isolated from the transformant, shown as mutant AK120 in FIG. 7. This is because after integration of the BamHI digested construct 90 into the genomic DNA of strain HL330 at a BamHI site 100 the integrated construct 90 is flanked by BamHI sites 110 and 112 on the resulting DNA region 113. DNA was isolated from 48 transformants and digested with the BamHI enzyme and a Southern blot was probed with sequences specific for construct 90. 35 of these 48 DNAs from these transformants gave the 6.7 kilobase pair long construct 90 after digestion with BamHI. When the experiment was carried out with EcoRI digested construct 90 and transformation was carried out in the presence of the EcoRI enzyme, in 10 out of 14 cases a 6.7 kilobase pair long fragment was obtained. This result showed as in the case of yeast above that more than 70 percent of these transformation events were mediated by restriction enzymes.

When the DNA of these transformants was digested with other restriction enzymes many different sized fragments were obtained for 10 of these transformants indicating that each of these integration events happened into a different BamHI or EcoRI site. When the BamHI digested construct 90 was transformed in the presence of Sau3A the same increase in transformation frequency was obtained as was obtained in the presence of BamHI. However, BamHI digested construct 90 in the presence of EcoRI did not result in enhanced transformation efficiency. The BamHI and the Sau3A enzymes generate the same 5' overhanging single stranded extensions GATC whereas EcoRI creates an AATT 5' overhang. Therefore, it is likely that the same single stranded overhang is important in the process. Other enzymes were successfully used. These include ClaI and BglII. However, there is no doubt that still other enzymes will be useful in the same way.

Large scale transformations were carried out to assess the feasibility of using restriction enzyme mediated integration to obtain developmental mutants in Dictyostelium. Construct 90 was digested with BamHI or EcoRI and used to transform strain HL330 by electroporation in the presence of BamHI or EcoRI respectively. Sau3A was also used with BamHI digested vectors. The transformants were screened for morphological defects as they grew and developed clonically on bacterial plates. Of a total of about 6000 primary transformants, sixteen were found to arrest development at specific stages or have aberrant terminal morphology. Four mutants were aggregation deficient, 4 aggregated partially, 2 formed tight aggregates, but failed to progress to apical tip formation, and 6 had aberrant terminal fruiting bodies. The electroporation of cells in the presence of BamHI or EcoRI in the absence of construct 90 produced no mutants in over 2500 clones analyzed. Therefore for applicants process it is important that the digested construct 90 or any similar construct 90s together with the respective restriction enzyme be used.

Figure 7B:
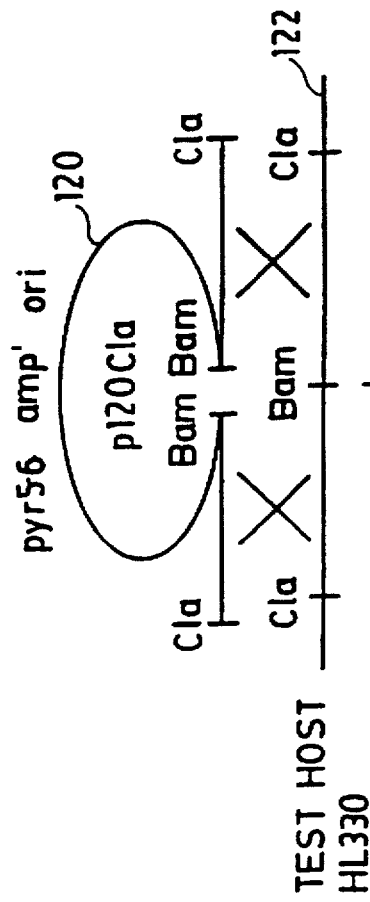
FIG. 7 is a schematic of the integration event of the plasmid DIV2 into one possible chromosomal BamHI target site, the cloning of that target site and the reintroduction of the same mutation into another strain.

Referring again to FIG. 7, proof that the insertional events were the cause for the observed phenotypes was obtained by reintroducing disrupted insertion sites back into the parental strain as shown. To do this, the integrated construct 90 was recovered with varying amounts of flanking DNA from the mutant strains. To clone these fragments in *E. coli* 0.5 micrograms of genomic DNA from the insertion mutant, AK120 in case of FIG. 7, was digested with enzymes that do not cut within construct 90 and produce a vector containing fragment of more than 15 kilobase pairs in size, ClaI in the case of FIG. 7. The ClaI restriction enzyme digests at points 114 and 116 to give rise to a DNA fragment including construct 90. The DNA was purified, dissolved in 10 microliters of sterile water and then brought up to 0.5 ml ligase buffer as recommended by the supplier, the aforementioned Life Technologies Inc. 10 units of T4 DNA ligase (Life Technologies) was added and incubated for more than 12 hours at 12° to 15° C. Thereafter the ligation products were precipitated with ethanol and dissolved in 40 microliters of sterile water and 2–6 microliters of SURE *E. coli* cells from Stratagene of 11099 North Torrey Pines Road, La Jolla, Calif. 92037 were transformed with the aforementioned gene pulser from BioRad as recommended by the supplier. In this way plasmid p120Cla of FIG. 7 was cloned. This plasmid was reintroduced into Dictyostelium DNA as shown in FIG. 7B by homologous recombination. The plasmids were linearized with the restriction enzyme used in their cloning strategy, ClaI in case of FIG. 7 (to produce digested product 120) and reintroduced in cells of strain HL330 as described above and incubated as described above. It was hoped that homologous recombination would result in replacement of the endogenous gene 122 with the disrupted copy 120 to yield the mutant locus 124 in a high proportion of the transformants. This was carried out for four different mutant strains. In each case the mutant phenotype of the original insertion was recovered in a substantial percentage of the transformants. These results demonstrate that the insertions carried in these four strains each disrupt a developmentally required genetic element.

The region surrounding the insertion site was mapped in several of the resulting transformants. Each of the transformants that showed the mutant phenotype (mutant AK227 in FIG. 7) had the same genomic structure as the original mutant insertion strain (mutant AK120 in FIG. 7).

As will be apparent to those skilled in the art, the aforementioned description of one preferred construct is only one of many within the scope of this invention. In addition, other restriction enzymes can be used. An especially useful subset thereof includes enzymes that are engineered to cut at specific designed sequences. In this way, one may insert genes into predesigned locations of the genome with enzymes that cut only once in the genome.

Applicant's process has been shown in other portions of this specification to be applicable to the yeast *Saccharomyces cerevisiae* and to the slime mold *Dictyostelium discoideum*. These two very different organisms are merely illustrative of the many that may be used in this process. Thus, by way of illustration and not limitation this process may be used in plants, in mammalian cells and the like.

In yet another preferred embodiment, mammalian cells are used and the genetic events shown in FIGS. 1 to FIG. 5 are constructed in an equivalent fashion with mammalian cells. The construction of such a system requires selectable markers for transformation of mammalian cells which are available. Without limitation these selectable markers include the herpes simplex virus type 1 gene coding for thymidinekinase, H-TK, the neomycin (neo) gene of Tn5, which confers G418 resistance to transformed mammalian cells and the bacterial plasmid encoded hygromycin-B-phosphotransferase (hph) gene which confers resistance to hygromycin-B in mammalian cells and the like. For a description and a summary of the usefulness of these genes see e.g., a book by R. Kucherlapati entitled "Gene Transfer", Plenum Press, New York. The H-TK, neo and the hph genes are freely available to those skilled in the art and are present in the collection of GeneBioMed, Inc. Transformation of mammalian cells can be accomplished by $CaPO_4$—DNA mediated gene transfer, and methods to derive single copy integrants have been described see e.g., the aforementioned book by Kucherlapati.

The systems in mammalian cells are constructed by replacing the genes LEU2, TRP1, URA3, LYS2, and the like of yeast with the aforementioned selectable dominant markers HTK, neo and hph and the like of mammalian cells. The HTK system allows one to select positively for the TK+ phenotype on medium supplemented with hypoxanthine, aminopterin and thymidine (HAT medium) and negatively for the TK⁻ phenotype on medium supplemented with hypoxanthine and bromodeoxyuridine (HBu medium) so that it allows determination of recombination events by selection for the presence of the gene. The neo gene can be selected for on medium supplemented with G418 and the hph gene can be selected for on medium supplemented with hygromycin-B.

Figure 8:
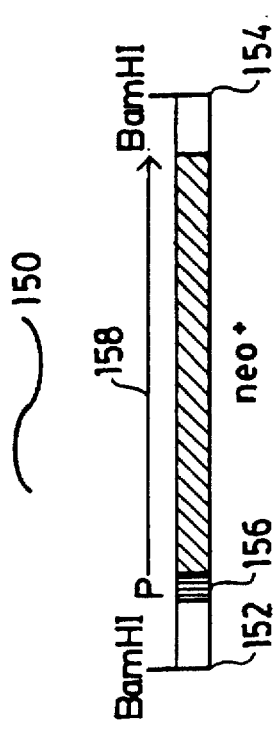
FIG. 8 is a schematic of the constituents of yet another preferred embodiment, the functional neo gene which may be used in applicants process for mammalian cells.

FIG. 8 illustrates construct 150, the neo gene which may be used in mammalian cells. Construct 150 is widely available to those in the art. Construct 150 is comprised of the open reading frame of the neo gene and sequence 156 which are promoter sequences. The direction of transcription is indicated by arrow 158. This fragment is flanked by BamHI sites at points 152 and 154. This fragment may be used in applicant's process in the same way in mammalian cells as construct 10 of FIG. 1 in yeast except that the homologous genomic DNA sequence does not have to be removed, since the majority of recombination events in mammalian cells are of the nonhomologous type. All other construct 150's fall within the scope of this invention as long as used in applicant's process. By way of illustration but not limitation these alternative construct 150's may contain the Htk gene, the Hprt gene, the Ada gene and the like.

Figure 9:
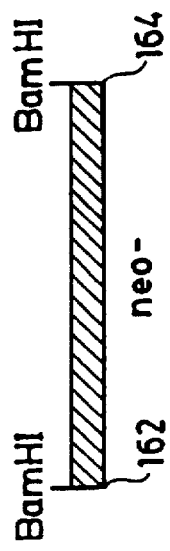
FIG. 9 is a schematic of the constituents of yet another preferred embodiment, the nonfunctional promotorless neo gene which may be used in applicants process for mammalian cells.

FIG. 9 illustrates construct 160 which contains the open reading frame of the neo gene which may be used in mammalian cells in applicants process. This fragment is flanked by BamHI sites at points 162 and 164. Construct 160 may be used in mammalian cells in the same way as aforementioned for construct 40 in applicant's process in yeast, except that the homologous genomic DNA sequence does not have to be removed, since the majority of recombination events in mammalian cells are of the nonhomologous type. All other construct 160's fall within the scope of this invention as long as used in applicant's process. Alternative construct 160's may contain the Htk gene, the Hprt gene, the Ada gene and the like.

Figure 10:
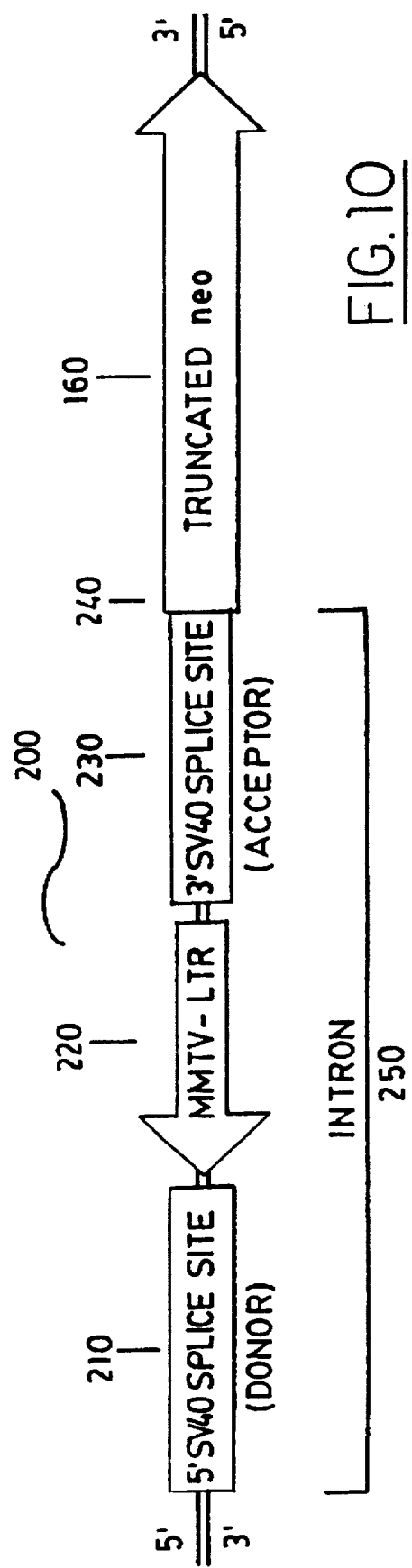
FIG. 10 is a schematic of the constituents of yet another preferred embodiment, the nonfuntional promoterless neo gene containing an intron adjacent to its 5' end; said intron is comprised of an inducible promoter acting in the opposite direction of the truncated neo gene.

Referring now to FIG. 10 another preferred embodiment of the present invention is shown. The embodiment described herein is a conditional mutagenic fragment which inserts into the chromosome via either illegitamate recombination or restriction enzyme mediated integration as described above. Mutations that are detected with this fragment are within expressed genes.

FIG. 10 shows the design of this fragment. There are three main features of this construct: 1. a truncated neo gene, fragment 160, as described above, 2. an inducible promoter 220 for transcription operating in the opposite direction of the neo gene fragment, and 3. splice sites 210 and 230, surrounding the inducible promoter sequence.

FIG. 10 provides an example of one conditional mutagenic fragment within the scope of this invention. This construct includes the promoterless neo gene, fragment 160, which is directly adjacent to the acceptor splice site sequence 230 which creates the 3' end of intron 250. Within intron 250 lies the inducible promoter sequence, fragment 220, which must run in the opposite direction of fragment 160. Here, the inducible promoter is mouse mammary tumor virus MMTV-LTR, which is inducible in response to dexamethasone. This promoter is found commerically in expression vectors as in Clonetech's pMAMneo (cat#6104-1) and pMAMneo-CAT (cat#6141-1). Studies in 1989 by C. Sardet et al in "Molecular Cloning, Primary Strcuture, and Expression of a Human Growth Factor-Activatable Na+/H+ Antiporter" published in Cell, volume 56 on pages 271 to 280 describe that the MMTV-LTR promoter induces five fold after a 24 hour exposure to 1 micromolar dexamethasone in mouse L cells. The promoter MMTV-LTR described here is illustrative and not limiting. Other inducible promoters such as the metallothionine promoters inducible by metal ions hormone inducible promoters and the like are within the scope of this invention. The inducible promoter 220 is bordered by an acceptor splice site, as mentioned above, and a donor splice site. The sense consensus sequences of these splice sites must be on the opposite strand to the sense sequence of promoter 220. Illustrative examples, yet not limiting thereof, of splice junctions are from SV40 sequences coding for T antigen and mouse β-globin as published by G. Chu and P. A. Sharp in 1981 in an article entitled "A gene chimaera of SV40 and mouse β-globin is transcribed and properly spliced" in Nature, volume 289, pages 378 to 382. Other donor and acceptor splice sites lie within the scope of this invention.

The inducible promoter provides a mode known to those skilled in the art to control transcription levels under different conditions, such as specific compound concentrations or variations in growth media and temperature. The transcription products from promoter 220 will encode antisense RNA for the sequence that lies downstream. As know to those skilled in the art, antisense MRNA inhibits the translation to protein of the corresponding sense mRNA. Crowely et al in a 1985 publication entitled "Phenocopy of dicoidin I-minus mutants by antisense transformatiion in Dictyostelium" in Cell volume 43: pages 633 to 641 along with other research groups have observed that the mutant phenotypes expressed in cells encoding a certain gene's antisense mRNA are analogous to those seen in cells which have experienced deletions in the gene or have had the encoded proteins' function blocked through biochemical methods. Hence, the construct described here will allow conditionally controlled production of antisense mRNA and expression of corresponding mutant phenotypes.

In the first step in the use of construct 200 mammalian cells are transformed with this DNA fragment and selection is applied for G418 resistance that selects for expression of the neomycin gesistance gene. This first step selects from all possible integration sites for integration of construct 200 into an expressed gene. Expression and functioning of the neomycin gene occurs since the inducible promoter 220 is spliced out in this direction of the transcript. In the second step of this process, a compound is added or conditions are applied that lead to induction of the promoter 220 which in turn leads, to the production of antisense RNA from the gene into which fragment 200 has integrated. This antisense RNA will inhibit the translation of messanger RNA from the other allele of this gene on the other homolog thereby producing a conditional mutation.

The splice sites, fragments 210 and 230, which border the inducible promoter sequence described above, provide a mode which will increase the screening efficiency of properly integrated genes. As known to those in the art and as described in B. Lewin's text Genes IV on pages 578 to 609, DNA sequences coding for eukaryotic protein are interupted by noncoding sequences called introns. After transcription, the intervening introns are removed via splicing to create a mature mRNA, which is then transported to the cytoplasm to be translated into protein. The minimal sequence needed for splicing appear at the splice sites, which are at the 5' and 3' ends of the intron. A consensus sequence of: AGGU(A)AGU ... intron ... (U/C)$N_{11}$CAGG 5' splice site (donor) 3' splice site (acceptor) where the highlighted nucleotide are essentially invarient, has been found for splice sites through a comparison of a large number of examples. The splicing of the MRNA which corresponds to the antisense strand of the inducible promoter, fragment 220, removes codons for unnecessary amino acids into the fragment-160 fusion protein sequence, insertions that would cause protein misfolding and general protein unstablilty.

It has been shown that construct 10 works for applicant's process. It has been shown that construct 40 works for applicants process. Construct 46, 150, 160 and 200 also falls within the scope of this invention. In addition, all other constructs 10, 40, 46 with a variety of different genes fall within the scope of this invention as long as the homologous genomic sequences have been removed or there are no extended homologous genomic sequences present. In addition, constructs 150 and 160 fall within the scope of this invention as long as a restriction enzyme or any other enzyme has been added and the events are restriction enzyme or enzyme mediated and/or the construct is used for screening an agent to detect its potential to induce genome rearrangement.

So far systems to select for illegitimate recombination events based on transformation have been described. The construction of a selective system for illegitimate integration independent of transformation in *Saccharomyces cerevisiae* is described below. This system has the advantage that every cell contains the system as compared to the transformed cells only in the methods described above. Therefore, a much higher number of illegitimate recombination and/or restriction enzyme mediated recombination events will be obtained. As apparent to those skilled in the art, the following description of one preferred construct is only one of many within the scope of this invention. We constructed the substrate plasmid used in the selective system for IR and we showed that it works for our purpose. The strategy for the selective system is as follows.

I will first describe the strategy and the construction of the system. This system is designed so that no homology exists between the integrating fragment and the genome of the host strain. The system operates with the I-SceI endonuclease. No sites for I-SceI exists in the genome which facilitates the construction. I-SceI is a site specific endonuclease encoded by a mobile group I intron of yeast mitochondria. Colleaux et al. (1988, described in a paper entitled "Recognition and cleavage of the intron-encoded omega transposase" published in Proc. Natl. Acad. Sci. USA 85 on pages 6022 to 6026) artificially constructed a version of the I-SceI enzyme with the nuclear genetic code. The I-SceI enzyme recognizes a 18 base-pair long nonpalindromic sequence and does not have any cutting site in the nuclear DNA of *S. cerevisiae*. This, as well as the fast that the I-SceI enzyme and a linker with the cutting site is commercially available convinced us to to use the I-SceI gene. Furthermore, the nuclear version has been shown to cut at a single artificially introduced site in vivo (Plessis et al. 1992; and Dujon, personal communication). A promoterless ura3 allele flanked by I-SceI sites on a plasmid has been constructed and a GAL inducible I-SceI gene see Plessis et al. in a publication entitled "Site specific recombination determined by I-SceI, a mitochondrial group I intron-encoded endonuclease expressed in the yeast nucleus" published in Genetics, volume 130 on pages 451 to 460 (1992). The GAL inducible I-SceI gene is integrated into the genome and the promoterless ura3 gene is present on plasmid YEplac181 a 2 mm LEU2containing plasmid. After a shift from a glucose or, even better, a raffinose-containing medium (which allows for faster induction) to a galactose-containing medium, the ISceI gene is expressed and cuts the sites flanking the ura3 fragment. The ura3 fragment thus integrates into the genome in nonhomologous positions. When the ura3 fragment integrates into a position where it is fused in frame to another gene, the URA3 gene is expressed and the cell is able to grow on medium lacking uracil.

The plasmid used in the selective system has been constructed and shown to work for this purpose after in vitro digestion with I-SceI and transformation into strain RSY12. A BamHI fragment containing the promoterless ura3 (see above) was cloned into the multicloning site of plasmid YEplac211, a 2 mm. LEU2 vector. The resulting plasmid pWY112 was partially digested with BamHI and a commercially available linker with BamHI compatible sticky ends containing the I-SceI site was ligated into the BamHI site. We have determined that only one of the two orientations of the I-SceI site will result in an open reading frame from the I-SceI site in frame with the promoterless ura3 gene. A plasmid pWY114 containing the I-SceI site in the correct orientation in front of the promoterless ura3 allele was identified by restriction mapping and by DNA sequencing. This plasmid was further digested with AatII that cuts on the other side of the ura3 allele and the pUC portion of the vector. AatII-BamHI adapters wereligated to the I-SceI linker and this construct was ligated into the AatII site of plasmid pWY114 to give rise to plasmid pWY132. Digestion of plasmid pWY132 with I-SceI results in two fragments one of them containing the promoterless ura3 allele with the pUC portion. The position of the second I-SceI site was chosen such that the promoterless ura3 allele can integrate into the genome leaving behind the LEU2 portion and the 2 mm. portion of the vector. Thus, the integrated plasmid, since it contains the pUC portion, can be easily cloned together with the genomic target site.

The selective system has many other uses which are within the scope of this invention. For instance it may be used as a screen to isolate new mutants. Different colonies may be grown up on nonselective medium and then transferred to medium containing galactose to induce the HO endonuclease. Thereafter, the colonies can be replica plated onto medium lacking uracil. Colonies showing a higher or lower frequency of papilation can be picked and used to determine more accurately the frequency of illegitimate recombination from a liquid culture. Putative mutants showing a higher or lower frequency of illegitimate recombination can be isolated. EMS will be used to obtain temperature-sensitive mutations in essential genes. The mutants that are obtained can be examined for their effects on targeted integration, meiosis, UV and X-ray sensitivity, allelism to known recombination genes, and, in case of UV or X-ray sensitivity, allelism to known DNA repair genes, effects on. other types of intrachromosomal exchange, interchromosomal mitotic recombination and meiotic recombination.

If the above isolated mutations identify new alleles, the wild type genes can be cloned. There is a substantial difference in targeted versus nontargeted integration between $S.$ $cerev.$ and other organisms. For instance, in yeast, targeted integration is $10^4\times$ more frequent than nontargeted. This ratio is reversed for mammalian cells.

Mammalian genes involved in illegitimate recombination have obvious applications for reducing the frequency of illegitimate recombination to improve the ratio in favour of targeted integration. This is achieved by deleting these genes involved in nonhomologous recombination in mammalian cells or by producing antisense RNA from specific vectors.

An additional approach can be used to directly clone functions involved in illegitimate recombination. Gene pools on multicopy plasmids or on plasmids with inducible promoters, can be used to screen for sequences showing an increased level of illegitimate recombination. The advantage of this approach is that in addition sequences from other organisms can be screened. Because of the high efficiency of illegitimate recombination in mammalian cells, the isolation of sequences from mammalian cDNA yeast expression libraries that increase the frequency of illegitimate recombination in yeast should work. These sequences can then be characterized and can be used in mammalian cells to decrease the level of illegitimate recombination as described above. This technology will help to increase the frequency of homologous recombination (targeted integration) for uses in gene targeting and gene therapy.

The abovementioned constructs and the selective system or equivalent constructs and systems may be used to detect the presence of chemicals which cause genome rearrangement.

It appears that constructs of this invention may be substantially more sensitive in detecting carcinogenic chemicals than are prior art short term tests. The process of this invention can be used to screen for any agent which is suspected of causing genome rearrangement. The agent may be in gaseous, liquid, or solid form; it may be an electromagnetic wave; it may be an element or a compound; or it may be some combination thereof.

The suspected agent may be radiation such as, e.g., radiation with a frequency of from $3\times10^9$ to $3\times10^{22}$. Some of the radiations which are suspected of causing genome rearrangement include, by way of illustration, ultra-violet light, X-rays, gamma-rays, and the like. Often the suspected agent may be a combination of one or more forms of radiation with one or more other agents. Thus, for example, the interaction of X-rays with certain organic matter is believed to often create free radicals which interact with DNA and are believed to cause DNA lesions.

The suspected agent may be any material or form of energy. Some of the agents which the process of this invention can be used to screen are described in a book by H. A. Milman and E. K. Weisburger entitled "Handbook of Carcinogen Testing", (Noyes Publications, Park Ridge, N.J., 1985), the disclosure of which is hereby incorporated by reference into this specification.

In one preferred embodiment, the agent to be tested is one which is not carcinogenic by itself but becomes carcinogenic when metabolized. These agents are often referred to as "procarcinogens" and are described, e.g., on pages 130–149 of said Milman and Weisburger handbook.

When a suspected procarcinogen is to be tested in the process of this invention, one should first provide a medium designed to simulate the metabolism the procarcinogen is subjected to in the body. Thus, for example, for a procarcinogen which can be metabolized in the presence of liver enzymes, one can provide a medium comprised of liver enzymes.

By way of illustration, one can provide a medium comprised of 10 percent (by volume) of "S9" (a supernatant of liver homogenate which is described in the aforementioned paper by Ames et al. appearing at pages 347–364 of volume 31, (1975) of $Mutation$ $Research$ entitled "Method for Detecting Carcinogens and Mutagens with the Salmonella/Microsome Mutagenicity Test: and which, as is known to those skilled in the art, is commercially available.), 2 percent by volume of a solution comprising magnesium chloride and potassium chloride, 0.5 percent by volume of a one molar solution of glucose-6-phosphate, 4 percent by volume of nicotineamide adenine dinucleotide phosphate, 50 percent by volume of a 0.2 molar phosphate buffer with a pH of 7.4, and 35.5 percent by volume of water. This S-9 mix is described in detail in 1975 Ames et al. paper.

As those in the art are aware, the S-9 mix should be evaluated to determine that it is active. It is preferred that, when the procarcinogen is being evaluated, a control experiment utilizing the S-9 mix and a known procarcinogen is conducted to verify that the S-9 mix is active.

In this embodiment, the harvested yeast cells are incubated in the presence of both the S-9 mix and the suspected procarcinogen.

In the first step of this process, a viable strain of $Saccharomyces$ $cerevisiae$ yeast which comprises a plasmid or a DNA fragment inserted into its genome which does not show any extended homology to the genome. The provision of this species of yeast is described in the first portion of this specification.

It is preferred to grow the viable species of yeast in suitable growth medium in order to have a sufficient number of yeast cells so that the experimental data generated will be statistically significant. In order to generate a suitable number of the viable yeast cells, the cells should be grown in a medium which permits growth of the cells. Those skilled in the art are well aware of suitable media which will permit growth of the cells which did not undergo genome rearrangement.

A suitable medium for permitting growth of the cells which did not undergo genome rearrangement is "YEPD". This medium contains yeast extract (one percent, by weight), peptone (any of various protein compounds obtained by acid or enzyme hydrolysis of natural protein, which is present in a concentration of 2 percent, by weight), dextrose (2.0 percent by weight), agar (2 percent by weight), and water. For each and every one of the constructs described in FIGS. 1–5, this medium permits the growth of all cells. Other such media known to those skilled in the art also may be used for this purpose such as, e.g., "synthetic complete medium".

Synthetic complete medium contains yeast nitrogen base without amino acids and with ammonium sulfate, (0.67 percent, by weight, which can be purchased from Difco Laboratories of Detroit, Mich., dextrose (2 weight percent), agar (2 weight percent), water, and the following amino acids and bases per liter of total solution: 20 milligrams each of L-trypthophan, L-histidine hydrochloride, L-arginine hydrochloride, L-methionine, L-isoleucine, L-tyrosine, L-lysine hydrochloride, adenine sulfate, and uracil; 30 milligrams per liter of total solution of L-leucine; 350 milligrams of L-threonine per liter of solution; and 75 milligrams per liter of L-valine. It is recommended that the use of the aforementioned selective system or similar systems within the scope of this invention may include incubation in medium containing galactose instead of glucose before, during or after exposure of the cells to the agents to be tested.

Other suitable growth media can also be used. Thus omissions, and/or additions may be made in the concentrations and/or the compositions of the media described above without adversely affecting their performance.

After cells containing the construct of this invention have been grown to a suitably large number, it is preferred to purify the cells so obtained by means well known to those in the art. Thus, for example, one can collect cells by centrifugation or filtration; see, e.g., the article by F. Sherman et al. Other suitable separation processes also can be used. Optionally, the yeast cells may be washed with suitable solution(s).

It is preferred that, after the yeast cells have been harvested, they are counted in order to determine the number of yeast cells per unit of buffered solution. Conventional means well known to those skilled in the art can be used to count the yeast cells. Thus, by way of illustration, one can use a hemocytometer (a conventional means of counting red blood cells).

It is preferred to conduct a preliminary experiment to determine those concentrations of the agent to be tested which should be evaluated in the main experiment. Yeast cells are exposed to a wide range of concentrations of the agent to be tested to determine its cytotoxicity.

Suitable concentrations of the agent are used for its evaluation. Several portions of the harvested yeast cells are used in the experiment. One portion, which is otherwise treated in exactly the same way as the exposed portions, is not exposed to the agent. The other portions of the harvested yeast cells are exposed to the agent at various concentrations. Alternatively, and/or additionally, controlled-variable tests can be conducted with various concentrations of the yeast cells as well as various concentrations of the agent. As is known to those skilled in the art, the concentration of the yeast cells might influence the effect of the agent in one or more ways; thus, for example, a dense solution of yeast cells might shield irradiation more effectively than a dilute solution.

The separated yeast cells can be exposed to the agent to be tested by various means. In one embodiment, the yeast cells are mixed with a buffer before such exposure. In another embodiment, the yeast cells are mixed with a buffer, and the mixture is then plated directly onto the selection medium before being exposed to the agent. In yet another embodiment, the yeast cells are grown in a growth medium (such as one or more of the media described above which permit the growth of the cells which have not undergone genome rearrangement) in the presence of the agent to be tested.

The cells may be grown in the presence of the agent in logarithmic phase cultures. In one embodiment, for each of the test strains, a cell suspension of $2 \times 10^6$ cells per milliliter medium be prepared from a logarithmic phase culture pregrown in liquid medium. The whole mix is aliquoted into portions of 5 milliliter into disposable plastic tubes in the presence of the agent to be tested, the tubes are sealed and shaken continuously for several hours.

When the yeast to be used is mixed with a buffer, a suitable buffer which is compatible with the agent to be tested should be used. Thus, for example, nitrous acid needs an acidic pH to be a mutagen; and the buffer chosen for the yeast cells thus should be acidic.

When the yeast cells are to be plated upon a suitable selection medium and exposed to the agent, a medium which is both compatible with the agent and which promotes selection for genome rearrangement should be used.

The yeast cells are then exposed to the agent or agents to be tested. In general, the exposure is conducted under conditions and for a time sufficient to simulate the environment which is being tested for. Thus, e.g., a wide range of reagent concentrations and exposure times is disclosed in said Milman and Weisburger book; they all may be used in the process of this invention under suitable circumstances.

The exposed yeast cells are characterized by comprising a plasmid or an integrated DNA fragment or being transformed with a plasmid or a DNA fragment absent any homology between the plasmid or DNA fragment and the genome of said yeast strain. The nonhomologous DNA integrates into the genome of said yeast strain and gives rise to an insertion which is identifiable, i.e., when they are present in suitable media they can be distinguished from cells which have not undergone th genome rearrangement. In one preferred embodiment, the gene rearrangement involved with the exposed yeast cells is an insertion. In another preferred embodiment, the genome rearranged, involved is a deletion or translocation. Regardless of whether the genome rearrangement occurs by insertion or deletion or translocation, the screening procedure described below can be used.

A selection medium is selected for the yeast strain which, after the yeast cells have been plated onto it and grown, enables one to identify those yeast cells which have undergone the specified genome rearrangement. Those skilled in the art are aware of many such growth media which facilitate the identification of such yeast cells.

Thus, by way of illustration and not limitation, many such media are described in F. Sherman et al.'s "Methods in yeast genetics, a laboratory manual" (Cold Spring Harbor Laboratory, Cold Spring Harbor, N.Y., 1986).

As those skilled in the art are aware, each construct requires a certain selection medium which will enable one to identify the cells which have undergone genome rearrangement.

By way of illustration, one can use uracil omission medium (medium lacking uracil) for a construct utilizing one gene in the uracil metabolic pathway for insertion etc. Thus, for example, uracil may be omitted from the synthetic complete medium described elsewhere in this specification to provide a medium which contains all growth factors except uracil. Likewise, for these constructs, one can use tryptophan omission medium for a construct utilizing one of the genes in the tryptophan metabolic pathway.

After the yeast cells have been exposed to both the agent to be tested and the selection medium under the conditions of the test and have been incubated for some time period of about more than one day preferably at 30 degrees Celsius or any other temperature which allows growth of the yeast cells used, the number of colonies formed by cells which have undergone genome rearrangement are counted and compared with the number of colonies of yeast cells identical in substantially every respect with the exception of not having been exposed to the suspected carcinogenic agent. The rates of genome rearrangement for both the control and experimental samples are then compared.

The experiments should be conducted at different concentrations of the agent to be tested. If the rate of genome rearrangement of the yeast cells consistently increases with increases in the concentration and/or exposure time of the agent to be tested, then this is one indication that such agent causes genome rearrangement and might be carcinogenic. If, additionally, the rate of genome rearrangement in the presence of one or more concentrations of the agent is substantially greater than the rate in the absence of the agent, this is yet another indication that such agent might be carcinogenic. It should be noted that the rate of increase of genome rearrangement is not necessarily linear with every agent and that some agents might show a lower rate of genome rearrangement with higher concentrations than with lower concentrations. As long as, for at least a certain range of the agent's concentrations, the rate of genome rearrangement is substantially greater than the rate obtained with the control samples, there is some indication that the agent might be carcinogenic.

Several factors influence what will constitute a "substantially greater" rate of genome rearrangement in the process. In the first place, the greater the number of yeast colonies obtained in the experiment, the lower the difference must be in order to be "substantial". In the second place, if a plot of the rate of genome rearrangement versus concentration of the agent to be tested produces a curve in which, for any two points, the rate of genome rearrangement for the higher concentration of agent is at least equal (and preferably higher than) the rate of rearrangement obtained with the lower concentration, the increase might be regarded as substantial. This curve is to be distinguished from a curve obtained in which the rate of genome rearrangement does not consistently increase or at least stay the same as the concentration of the agent is increased. As those skilled in the art are aware, the yeast cell colonies can be counted by conventional counting means. Thus, for example, one may count these colonies by hand. Alternatively, one may utilize commercially available counters such as, e.g., the Artek counter.

The data obtained from the counting of the yeast cells may be evaluated by means well known to those skilled in the art. Thus, for example, one may use the procedures described in an article by B. Kunz and R. Haynes published in a book by J. Strathern entitled "The molecular biology of the yeast Saccharomyces", (Cold Spring Harbor Laboratories, Cold Spring Harbor, N.Y., 1981). Thus, e.g., one may use the procedures described in an article by F. Eckardt and R. H. Haynes entitled "Quantitative measures of mutagenicity and mutability based on mutant yield data", Mutation Res 74:439–458 (1980). The disclosure of these articles is hereby incorporated by reference into this specification.

EXAMPLES

The following examples are presented to illustrate the preferred embodiments of this invention but are not to be deemed limitative thereof. Unless otherwise stated, all parts are by weight and all temperatures are in degrees centigrade.

Example 1 relates to the construction of strain RSY12 used in one preferred embodiment in applicant's process. The prior art procedures are illustrated in the Examples by reference to prior art publications, each of which is hereby incorporated into this specification.

EXAMPLE 1

Construction of the Deletion of URA3:

Referring to FIG. 2 construct 20 can be obtained by digesting plasmid pJL202 with the restriction enzymes XhoI point 30 and NotI point 32 by means well known to those skilled in the art and described above. Plasmid pJL202 is freely available and has been constructed by Joachim Li in Jef Boeke's laboratory at the aforementioned address.

E coli strain SF8 was transformed with plasmid pJL202. E. coli transformation was started with an overnight culture of strain SF8 in LB medium. It is believed that strain SF8 has the following genotype: hsdr–, hsdm–, recA1, supE44, lacz4, leuB6, proA2, and thi1. 5 ml of Luria Broth (LB) medium containing 10 grams of tryptone, 5 grams of yeast extract, (both ingredients obtained from Difco Laboratories of Detroit, Mich.) 5 grams of sodium chloride per liter of medium was inoculated with a single bacterial colony, incubated overnight at 37° C. in a New Brunswick incubator with vigorous shaking. 0.3 ml of this culture were inoculated into 30 ml of fresh LB medium and incubated under vigorous shaking at 37° C. until the culture reached an OD at 600 nanometers of 0.6. The culture was chilled by placing onto an ice water bath and thereafter the cells were collected by centrifugation at 6.000 rounds per minute (hereinafter called rpm) in a Sorvall centrifuge for five minutes. In the ice water bath one milliliter of an ice cold solution of 50 millimolar calcium chloride was added to the cell pellet and mixed. Ten microliter of the ligation mix was added to 5 ml. of a solution of one molar calcium chloride and 85 ml. of buffer containing 10 millimolar of the aforementioned Tris-base and one millimolar EDTA adjusted to pH 8.0 with hydrochloric acid (this buffer is hereinafter called Tris/EDTA pH 8.0). 0.2 milliliter of cell suspension was added to the DNA solution in small cooled plastic tubes. The solution was mixed gently and left on ice for 30 minutes. Thereafter the suspension was heated to 45° C. in a water bath for two minutes and then placed again into the ice bath to cool down. Three milliliter of LB medium was added and the tubes were incubated at 37° C. for two hours. Thereafter the cells were collected by centrifugation at 6.000 rpm for 5 minutes and the cell pellet suspended in 0.5 ml LB medium. 0.1 milliliter were plated onto each of LB plates containing 100 micrograms per milliliter of Ampicillin (obtained from Sigma Chemical Company).

Ampicillin resistant colonies were isolated and plasmid DNA was isolated from them as a modification of the boiling method, published by Holmes and Quigley in a publication entitled "A rapid boiling method for the preparation of bacterial plasmids." Anal. Biochem. 114:193–197 (1981). One milliliter of E coli culture containing the plasmid of interest was grown overnight in LB medium containing ampicillin. The cells were transferred to a 1.5 ml Eppendorff tube and spun down in a microfuge. The cells were resuspended in 0.4 ml of STET buffer consisting of 1 molar Tris–base adjusted to pH7.5 with hydrochloric acid, 20% triton (purchased from Sigma Chemical Company), 50% sucrose and 0.5 molar EDTA. Further 40 ml. of a solution containing 10 mg of lysozyme (purchased from the aforementioned Sigma Chemical Company) per milliliter of double glass distilled water was added and the solution mixed. The solution was further boiled for 50–60 seconds and immediately thereafter placed in an ice-waterbath for 1 minute. The solution was spun in a microfuge for 10 minutes at four degrees Celsius and thereafter the resulting pellet was removed with a sterile toothpick. Further 500 milliliter of cold (−20 degrees Celsius) isopropanol was added the content mixed by inverting the tube several times and the tube was thereafter left in the freezer (−20 degrees Celsius) for 10 minutes. The solution was furthermore spun for 3 minutes in the microfuge at four degrees Celsius and afterwards the supernatant discarded; the pellet was resuspended in 50 ml. of a Tris/EDTA buffer adjusted to pH 8.0 with hydrochloric acid and 50 ml. of a solution consisting of 5 molar lithiumchloride and 50 millimolar Tris/EDTA pH 8.0 was added. The content of the tube was furthermore mixed and incubated in an ice-waterbath for 5 minutes. Thereafter the content was spun in a microfuge for 5 minutes at 4 degrees Celsius and the supernatant was removed and placed into a new Eppendorff tube. Furthermore 200 ml. of cold Ethanol (−20 degrees Celsius) was added and after mixing of the content by inverting the tube several times the tube was left at −20 degrees Celsius for 10 minutes. After spinning of the tube for 3 minutes at 4 degrees Celsius the precipitate was washed with one half milliliter of 80% ethanol. After another spin for 3 minutes in the microfuge at 4 degrees Celsius the precipitate was dried in a desicator by means of creating a vacuum with a waterpump for several minutes until the precipitate was dry. Thereafter the precipitate was dissolved in 60 ml. of double glass distilled water or Tris/EDTA pH 8.0, depending on the further procedure. The resulting solution contained about 2 microgram of plasmid DNA which was cut with restriction enzymes to determine that the isolated colonies had the correct plasmid.

Thereafter plasmid pJL202 was isolated large scale from $E.\ coli$: 5 milliliter of LB medium with ampicillin was inoculated with a single bacterial colony, incubated overnight at 37° C. in a New Brunswick incubator with vigorous shaking. 2.5 milliliter of the overnight culture was inoculated into a two liter flask containing 500 milliliter of M9aa minimal medium: M9aa medium contained per liter of distilled water solution, 6 gram of sodium phosphate ($Na_2HPO_4$), 3 gram of potassium phosphate ($KH_2PO_4$) 0.5 gram of sodium chloride (NaCl), one gram of ammonium chloride ($NH_4Cl$) and 4 gram casaminoacids (obtained from Difco Laboratories). The medium was adjusted to a pH of 7.4, sterilized by autoclaving and after cooling the following solutions were sterilized by filtration and added, two milliliter of one molar magnesium sulphate ($MgSO_4$), 10 milliliter of 20% w/v glucose, 100 ml. one molar calcium chloride ($CaCl_2$) and one milliliter of 100 g/ml of Ampicillin. The culture was vigorously shaken at 37° C. until it reached an OD at 600 nanometer of 0.6 and 65 milligram of chloramphenicol (purchased from Sigma Chemical Comp.) were added and the culture was further incubated for another 14 hours in the same way. The cells were separated by centrifugation in a GSA rotor for 10 minutes at 5000 rpm in a Sorvall centrifuge. Thereafter the cells from one liter initial culture were resuspended in 100 ml TS buffer containing 10% sucrose and 0.05 mol Tris-base adjusted to pH 8.0 with hydrochloric acid. The cells were again collected by centrifugation as described above and were chilled at 0° C. in an ice-water bath and resuspended in 10 ml ice cold TS buffer and transferred to a 50 ml flask. Two milliliters of a solution of 5 mg/ml of freshly dissolved lysozyme (obtained from Sigma Chemical Comp.) was added and the solution was mixed gently on ice for 10 minutes, four milliliter of a solution of ice cold 0.25 molar EDTA was added gently from the bottom of the flask and the mix left on ice for five minutes. 15 milliliters of triton lysis buffer consisting of a solution in distilled water of 10% triton X-100, 0.05 molar Tris base adjusted to a pH of 8.0 with hydrochloric acid, 0.05 molar EDTA were added and the solution was left for 10 minutes on ice. Thereafter the solution was spun in a SS34 rotor in a Sorvall centrifuge with 18.000 rpm at 4° C. for 60 minutes. The supernatant was collected and an equal volume of phenol, equilibrated with TE buffer, consisting of a solution in distilled water of 10 millimolar Tris base adjusted to a pH of 8.0 with hydrochloric acid and 1 millimolar EDTA, and an equal amount of chloroform was added. The solution was shaken for 3 minutes at room temperature and thereafter spun at 5.000 rpm in a SS34 rotor in a Sorvall centrifuge for 10 minutes and the supernatant was collected. The same procedure starting with the addition of phenol was repeated a second time and the water phases were joined and 17.5 milligram of sodium chloride was added per milliliter of solution. Absolute ethanol was added at twice the volume of the solution, the solution was gently mixed and left for 30 minutes in a freezer at −20° C. The solution was spun at 5.000 rpm for 5 minutes and thereafter the pellet containing the DNA was washed with 80% in distilled water of ethanol. The pellet was dried in an desiccator and was then dissolved in 5 ml TE buffer.

Another purification step using cesium chloride gradient centrifugation was added. To the TE solution 0.75 milliliter of a buffer consisting of one molar Tris base adjusted to a pH of 7.5 with hydrochloric acid and 0.1 milliliter of 0.5 molar EDTA in distilled water was added. 0.978 gram of cesium chloride per (weight of solution in gram plus 1.2) was added and the volume split in half and added each into a nitrocellulose centrifuge tube of a 50 Ti rotor, and 0.6 milliliter of 5 mg/ml of ethidium bromide was added to each and the solution topped up with paraffin, and the tubes were sealed. The tubes were mixed well and spun in a Beckman ultracentrifuge for 40 hours at 40.000 rpm at 20° C. The plasmid band was located using UV light and was removed with a syringe and transferred to a 30 ml centrifuge tube. The ethidium bromide was extracted five times with an equal volume of butan-1-ol which was saturated with TE buffer. The DNA was precipitated with three volumes of 70% ethanol in distilled water at −20° C. for one hour and collected by centrifugation at 10.000 rpm for 15 minutes in a SS34 rotor in a Sorvall centrifuge and dissolved in 0.5 ml TE buffer. The DNA solution was dialysed against TE buffer for 20 hours with changes of the buffer. The OD at 260 nanometer of the solution was determined and the concentration of DNA calculated. The yield was about 700 mg. of plasmid DNA.

Thereafter plasmid pJL202 was digested with restriction enzymes XhoI and NotI strain OD5 was transformed with the digestion mixture and HIS+ colonies were isolated on medium lacking histidine. Strain OD5 is freely available and has been obtained from Walter Spevak in the laboratory of Helmut Ruis, Department of Biochemistry, University of Vienna, Wahringerstrasse 49, 1090 Vienna, Austria.

To produce the URA3 gene disruption plasmid pJL202 was cut with XhoI and NotI to and strain OD5 was transformed with the DNA fragment to give rise to strain RSY12. Transformation of yeast was carried out by treating intact cells with lithium acetate as described by Ito et al. in a publication entitled "Transformation of intact yeast cells treated with alkali cations." J. Bacteriol. 153:163–168 (1983). 300 milliliter of a culture of strain OD5 in YEPD medium was grown overnight to 5 to $7 \times 10^6$ cells per milliliter from a fresh overnight culture. Cells were collected by centrifugation at 5,000 rpm for 5 minutes in a GSA rotor in a Sorvall centrifuge. The cells were resuspended in 1.5 ml of a solution of Tris/EDTA, pH 7.5 and 0.1 molar lithium acetate (obtained from Sigma Chemical company) and incubated for one hour at 30° C. with constant agitation. Five microgram of the digested plasmid pJL202 was mixed with 40 mg. sonicated salmon sperm carrier DNA (obtained from Sigma Chemical Company, dissolved in TE buffer, sonicated with a MSE 150 Watt Ultrasonic Disintegrator (obtained from Measuring and Scientific Equipment Ltd. Manor Royal, Crawley, Great Britain) for 10 minutes, extracted once with an equal volume of phenol, precipitated with twice the volume ethanol, dried under vacuum produced by a water pump and redissolved in TE buffer) in an Eppendorff tube and 0.2 ml of the cell suspension was added to the DNA. The suspension was incubated for 30 minutes at 30° C. with agitation in a New Brunswick controlled environment shaker. Thereafter 1.2 ml of a solution containing 40% polyethylene glycol 4000 (obtained from Sigma Chemical Company), TE buffer with a pH of 7.5 and 0.1 molar lithium acetate was added and the solution was gently mixed. The solution was incubated for another 30 minutes at 30° C. with agitation and thereafter heated for 7 minutes in a 42° C. waterbath. The cells were then collected by centrifugation in a Fisher microfuge for 5 seconds, washed twice with TE buffer with a pH of 7.5 and finally resuspended in one milliliter of TE buffer. 0.2 ml of this cell suspension was plated onto one petridish containing medium lacking leucine.

Single HIS$^+$ colonies were isolated and checked for their uracil phenotype. Uracil requiring colonies were checked by Southern blotting for the copy number and the presence of the integrated plasmid. A rapid procedure for preparation of small amounts of high molecular weight yeast DNA was used for screening large numbers of yeast colonies as described in a publication by Ciriacy and Williamson entitled "Analysis of mutants affecting Ty-mediated gene expression in *Saccharomyces cerevisiae*" which appeared in Mol. Gen. Genet. 182 on pages 159 to 163 (1981). Five milliliter of YPD medium was inoculated with a single colony of yeast and grown overnight to stationary phase. Cells were transferred to 15 ml sterile plastic centrifuge tubes and the cells were collected by centrifugation in a table top clinical centrifuge. Cells were resuspended in one milliliter of distilled water and transferred to an Eppendorff microfuge tube. The cells were resuspended in 0.4 ml of spheroblasting buffer containing 5 ml of SCE (one molar sorbitol, 0.1 molar sodium citrate, 6 millimolar EDTA with a pH of 7.0), 5 mg of zymolyase 5.000 (produced by Kirin brewery of Japan) and 40 ml. of mercaptoethanol and incubated in this buffer for one hour at 37° C. Thereafter 0.4 ml of a solution containing 2% sodium dodecyl sulfate in 50 millimolar Tris base with a pH of 8.0 and 10 millimolar EDTA was added and the tube was mixed gently until the solution cleared. 0.2 ml of 5 molar sodium chloride was added and the solutions were mixed by inverting the tube. The mix was left one hour at 0° C. to precipitate the DNA, the DNA was collected by centrifugation in a Fisher microfuge for ten minutes and the supernatant was discarded. 0.4 ml of TE buffer with a pH of 7.5 was added and the DNA dissolved. Thereafter 0.4 ml of a mix consisting of phenol, chloroform and isoamylalcohol at a ratio of 50:50:1 was added and the solutions mixed. The solutions were spun in a Fisher microfuge for 4 minutes and the supernatant was transferred into a new Eppendorff tube. 0.8 ml of absolute ethanol was added, the content was mixed and the mix was left in the freezer for 30 minutes. The precipitated DNA was collected by centrifugation for 5 minutes in a Fisher microfuge and the supernatant was discarded. The precipitate was dried in a vacuum and dissolved in 50 microliter of TE buffer. The ethanol precipitation was repeated once and about 10 microliter was used per restriction enzyme digest.

The DNA was digested for two hours with the restriction enzyme HindIII for two hours at 37° C. and loaded onto an agarose gel and electrophoresis was performed at 30 volts over night. The DNA was transferred to Gene Screen Membrane (purchased from New England Nuclear of 549 Albany Street, Boston, Mass. 02118) as indicated by the supplier for the Southern blotting procedure.

DNA of the aforementioned plasmid pM20 was radioactive labelled according to a procedure published by Feinberg and Vogelstein in a publication entitled "A technique for radiolabelling DNA restriction endonuclease fragments to high specific activity." Anal. Biochem. 132:6–13 (1983). The plasmid was linearized by digestion with BamHI, and the solution was boiled for 7 minutes. The reaction was carried out at room temperature by adding the following reagents in the stated order: distilled water to a total of 50 ml. of oligolabelling buffer containing solutions A, B and C in a ratio of 100:250:150. Solution A contained one milliliter of solution O (containing 1.25 molar Tris Buffer adjusted to a pH of 8.0 with hydrochloric acid, 0.125 molar magnesium chloride), 18 microliter of 2-mercaptoethanol, 5 ml. of desoxy adenosine triphosphate, 5 ml. of desoxy thymidine triphosphate, 5 ml. of desoxy guanosine triphosphate (each triphosphate at a concentration of 0.1 molar was previously dissolved in TE buffer (3 millimolar Tris base, 0.2 millimolar EDTA, adjusted to a pH of 7.0 with hydrochloric acid). Solution B contained 2 molar Hepes titrated to a pH of 6.6 with 4 molar sodium hydroxide. Solution C contained 90 optical density units per milliliter hexadeoxyribonucleotides (obtained from P-L biochemicals, Milwaukee, Wis.), 2 ml. of a solution of 10 mg per milliliter of bovine serum albumine (obtained from Bethesda Research Laboratories of Gaithersburg, Md.), the above prepared DNA, 5 ml. of [$^{32}$P]dCTP at a specific activity of 3000–4000 curie per millimol and 10 microcurie per microliter (obtained from Amersham Corporation of Arlington Heights, Ill.), 2 units of the large fragment of *Escherichia coli* DNA polymerase I (obtained from Bethesda Research Laboratory). The mixture was incubated for 2.5 hours and the reaction was stopped by addition of 0.2 ml of a solution consisting of 20 millimolar sodium chloride, 20 millimolar Tris base adjusted to a pH of 7.5 with hydrochloric acid, 2 millimolar EDTA, 0.25% sodium dodecyl sulfate, one micromolar deoxycytidine triphosphate. The labelled DNA was used for Southern hybridization as described by Williamson, et al. in a publication entitled "Transposable elements associated with constitutive expression of yeast alcohol dehydrogenase II" published in Cell 23:605–614 (1981). A prehybridization mix was prepared with 3 ml of distilled water 0.6 milliliter of filtered 10% sodium sarcosylate and 0.6 milliliter of one milligram per milliliter of sonicated salmon sperm DNA. The hybridization mix was prepared in the same way except that the labelled DNA was added and both mixes were heated to 85° C. for 5 minutes in a water bath and thereafter cooled to 0° C. in a ice water bath for 5 minutes. In a heat sealable plastic bag (Sears' Seal-n-Save) the prehybridization mix was added to the NEN Gene Screen membrane and after the membrane was moistened avoiding any air bubbles, the prehybridization mix was discarded. The hybridization mix was added and the bag was sealed and incubated over night at 65° C. The next day the bag was opened and the filter washed for 30 minutes in 500 ml of a solution per liter distilled water of 11.69 gram of sodium chloride, 16.09 gram of sodium phosphate (Na$_2$HPO$_4$×7H$_2$O), 0.37 gram of EDTA and 1% sodium dodecyl sulfate prewarmed to 45° C. The filter was washed in the same way for another 30 minutes in a solution per liter distilled water of 11.69 gram of sodium chloride, 16.09 gram of sodium phosphate (Na$_2$HPO$_4$×7H$_2$O), 0.37 gram of EDTA. Thereafter the filter was washed for 45 minutes in the same way in a solution per liter distilled water of 2.34 gram of sodium chloride, 3.22 gram of sodium phosphate (Na$_2$HPO$_4$×7H$_2$O), 0.074 gram of EDTA. Thereafter the filter was dried at 85° C. for four hours and for autoradiography exposed to a Kodak X-O mat X-ray film. The integrated plasmid formed one band in case of a single integrant and two bands in case of a multiple integrant.

One colony showing a single copy integration event was used as strain RSY12 was used for one preferred embodiment of applicants process. This step of construction of strain RSY12 is also published in the aforementioned paper by Schiestl and Petes published in Proc. Natl. Acad. Sci. USA 1991 vol. 88 on pages 7585 to 7589.

A modification of a procedure published by Hirt "Selective extraction of polyoma DNA from infected mouse cell cultures." J. Mol. Biol. 26:365–369 (1967) was used for purification of plasmid DNA from yeast.

EXAMPLE 2
Illegitimate and Restriction Enzyme Mediated Integration in Yeast using Construct 10

In order to determine whether yeast had a system allowing the integration of transforming DNA by nonhomologous recombination, a 1.2 kb BamHI DNA fragment encoding URA3 was transformed into a strain lacking these sequences. Different patterns of integration were observed. If the transforming solution contained the BamHI enzyme, the URA3 gene was integrated into BamHI sites in the genome. In the absence of the enzyme, the transforming fragment integrated into GATC sites in the genome. Other patterns did not integrate into GATC sites.

In the first series of experiments, the plasmid pM20 was treated with BamHI, resulting in a 1.2 kb URA3 fragment and a 2.7 kb pUC7 fragment. The solution containing the DNA and BamHI enzyme was transformed into the haploid strain RSY12 lacking URA3 sequences. A high efficiency yeast transformation protocol was used (up to $10^6$ transformants per mg of a plasmid capable of autonomous replication, see the aforementioned paper by Schiestl and Gietz, 1989). In this experiments, about five to 100 Ura$^+$ transformants per microgram of transforming DNA were obtained.

The resulting transformants were analyzed genetically and physically. Thirty were tested for stability of the Ura$^+$ phenotype. Cultures derived from each transformant were plated on medium containing 5-fluoro-orotic acid (5-FOA); ura3 mutants are 5-FOA resistant (see the aforementioned paper by Boeke et al., 1984). All transformants showed the same frequency (about $10^{-7}$) of 5-FOA$^R$ papillations as the wild-type strain OD5. This result indicates that the URA3 insertions are stable. Fifteen of the transformants were crossed to a ura3 strain of opposite mating type and the resulting diploids were sporulated by methods known to those in the art described e.g. in Sherman et al. "Methods in yeast genetics" Cold Spring Harbor Laboratory Press, CSH, New York. Five tetrads were dissected from each diploid. For all fifteen transformants examined, most tetrads segregated 2$^+$:2$^-$. This segregation pattern indicates that the wild-type URA3 gene is integrated into a single genomic site in each transformant. In addition, the same fifteen transformants were crossed to a haploid strain with a wild-type URA3 gene located at its normal location (chromosome V). Each transformant showed 4+:0$^-$, 3$^+$:1$^-$ and 2$^+$:2$^-$ tetrads in the ratios expected for unlinked markers. This result indicates that the URA3 genes in the transformants are not located at the "normal" location of URA3 on chromosome V.

DNA was isolated from the transformants and examined by Southern analysis as described above. The hybridization probe used in these experiments was pM20 which contains the URA3 gene and pUC sequences. When the DNA was treated with EcoRI (which does not cut within the 1.2 kb URA3 fragment) and analyzed, we found that most transformants contained a single strong band of hybridization, greater than 1.2 kb in size. The size of this band was different in different transformants. The URA3 gene in OD5 was located on an EcoRI fragment of 13 kb. The URA3 deletion strain RSY12, as expected, lacked this band. The observation that most of the transformants contain a single strong band of hybridization at different positions suggests that most of the transformants have a single URA3 insertion and the position of the insertions in the genome is different in different transformants.

When the DNA of 30 transformants was digested with BamHI and Southern hybridization was carried out, most (29 of 30) had a single fragment of about 1.2 kb that hybridized to URA3; this size is the same as that of the original BamHI URA3 fragment used for transformation. This result was unexpected since it indicates that the BamHI sites (GGATCC) at both junctions of the integrated URA3 gene are recreated. Even if the 5' overhanging ends (GATC) of the BamHI-cut fragment were filled-in in vivo by DNA polymerase, BamHI sites at both ends would not be recreated unless this fragment integrated between G and C residues.

To determine the mechanism of integration, the junctions of nine different URA3 integrants were sequenced and obtained the "target" sequences (the genomic sequence prior to the integration event) for four of these integrants. The URA3 insertions and flanking sequences were inserted into recombinant plasmids, recovered in yeast, transformed into E. coli, and sequenced using primers derived from the 3' and 5' ends of the URA3 gene. For all integrants, the URA3 sequences at the junctions were conserved and, as expected, BamHI sites flanked all insertions. The genomic sequences beyond the BamHI sites were different for different transformants.

Approximately 200 bp of genomic sequence was obtained for each junction. The GenBank database was searched for homology to each of these sequences. Although no homology was detected for eight of the insertions, the genomic sequences of one was identical to those of the previously sequenced SGA1 gene, a sporulation-specific glucoamylase gene (Yamashita et al., 1987, J. Bacteriology 169, pages 2142 to 2149). This "target" gene had a BamHI site at the position of insertion of the URA3 fragment. The comparison of the target gene and the integrant indicates that the BamHI URA3 fragment integrated without deletion or duplication of any sequences into the BamHI site in the target. Thus, the structures are consistent with a mechanism involving the simple ligation of the transforming fragment into a genomic BamHI site.

To test for the generality of this unexpected result, three other target sites were sequenced. The information concerning the flanking sequences was used to design pairs of oligonucleotides with the appropriate sequences to yield a DNA fragment of about 150 bp containing the "target" following application of the polymerase chain reaction (PCR) to DNA isolated from the strain OD5. The sequences of these oligonucleotides are given in Experimental Procedures. Using these primers, the genomic target sites were amplified representing the insertions. Sequence analysis indicated that all three target sites contained a BamHI site at the position of insertion of the URA3 fragment. In summary, in four of four transformants, the insertion of the BamHI URA3 fragment into the genome had the structure predicted for a conservative integration of the fragment into a BamHI site in the genome.

There are two interpretations of this result. First, the integration of the URA3 gene into the gene may be catalyzed by BamHI-mediated cleavage of chromosomal DNA, followed by ligation of the transforming fragment into the genome at the cleaved site. Alternatively, there may be a recombination event between the BamHI-generated ends of the URA3 fragment and BamHI sites in the genome that is not catalyzed by the restriction enzyme. To distinguish between these possibilities, the transformation properties of the BamHI URA3 fragment was examined in the presence and the absence of the BamHI enzyme. The plasmid pM20 was treated with BamHI and one-third of the sample was used to transform RSY12. The remaining twothirds was treated (as described above) with proteinase K and phenol in order to inactivate and remove the restriction enzyme. This sample was divided in half and, to only one of the two aliquots, the BamHI enzyme was re-added. Transformation was carried out with each of these aliquots and Ura$^+$ colonies were isolated. When the BamHI enzyme was readded, about seven times as many transformants were obtained than in the absence of the enzyme (15 transformants versus 101 transformants; 20 micrograms of DNA in each transformation).

DNA samples were prepared from the transformants, treated with BamHI, and examined by Southern analysis. Of the transformants obtained using DNA from the restriction digest with BamHI, 30% (3 of 10) had URA3 insertions with two flanking BamHI sites; URA3 genes with two flanking BamHI sites represent insertions of the URA3 gene into genomic BamHI sites. None of the transformants (0 of 9) obtained in the absence of the BamHI enzyme had two flanking BamHI sites. When the BamHI enzyme was added back to the URA3 fragments, 60% of the URA3 insertions (10 of 17) were flanked by two BamHI sites. To confirm that integration of the transforming fragment into BamHI sites was stimulated by the restriction enzyme, the experiment was repeated twice. In one of these experiments, the BamHI enzyme was inactivated by heating to 70° for 10 minutes, instead of by the proteinase K-phenol treatment. Summing the data from all experiments, it was found that the frequencies of transformants with URA3 genes with two flanking BamHI sites are: 80% (40/50) for BamHI URA3 fragments in the original BamHI digestion buffer (BamHI present), 5% (2/39) for BamHI URA3 fragments in the absence of BamHI enzyme, and 74% (34/46) for BamHI URA3 fragments with BamHI added back. The results indicate that the integration of the BamHI URA3 fragment into BamHI sites in the genome is catalyzed by the BamHI restriction enzyme. These events are the subject of one preferred embodiment of this invention, the Restriction Enzyme-Mediated event. The events obtained in the absence of the BamHI enzyme are the subject of another preferred embodiment, the illegitimate recombination events.

Integration Events in the Absence of BamHI: Illegitimate Integration:

As described above, integration events of the BamHI URA3 fragments that occurred in the absence of the enzyme usually did not regenerate BamHI sites flanking the insertion. To determine the nature of these enzyme-independent integration events, two of the integrants were sequenced and also the target sites for these integration events were determined. The methods used for the isolation and analysis of these sequences are identical to those described above for the REM events. In both integrants, the GATC sequence at the ends of the URA3 fragment was conserved, however, there was a BamHI site at only one of the four junctions. When the target sites for these integration events were determined, we observed that the BamHI URA3 fragment had integrated into a GATC sequence in the chromosome; for one transformant, three additional base pairs of homology were detected between the integrating fragment and the insertion site. Since the GATC target sequence is the same as that of the cohesive end in BamHI-treated DNA, these integration events have the structure expected for a conservative insertion of the BamHI URA3 fragment into genomic DNA with a staggered cleavage of a GATC site. Other events were also found which did not contain any GATC sequences at the target sites.

EXAMPLE 3
Restriction Enzyme Mediated and Illegitimate Integration in Yeast using Construct 40.

Construct 40 of FIG. 4 was used as described above to transform the aforementioned yeast strain RSY12. It has been previously shown in a paper by Alani and Kleckner 1987, Genetics 117 on pages 5 to 12 that a promoterless ura3 fragment can be fused in frame to a variety of genes and retains its activity, much like the lacZ gene of E. coli. Plasmid pRDG369 containing the ura3 allele missing its promoter and its transcription start site was constructed as described above in the description to FIG. 4. The ura3 fragment was amplified by the polymerase chain reaction (PCR) and cloned after digesting at BamHI sites that have been included in the primer design into the BamHI site of pUC19. This cloned fragment lacks the promoter and truncates the gene beginning at the 6th codon, similar to the construction of Alani and Kleckner. Plasmid pRDG369 was digested with BamHI and the yeast strain RSY12, lacking URA3 sequences, was transformed with the promoterless ura3 fragment in the absence of the BamHI enzyme. URA3+ colonies have been obtained at a frequency of about 2 per mg. of plasmid DNA in the absence of the BamHI enzyme and of about 20 per mg. of plasmid DNA in the presence of the BamHI enzyme. This experiment was repeated three times giving the same result. 16 of these URA3+ colonies were isolated, 2 from the experiment in the absence and 14 from the experiment in the presence of the restriction enzyme. Gene pools have been constructed and the promoterless ura3 gene has been cloned as described above for the URA3 fragment. Primers were designed to sequence from within the promoterless ura3 gene through the junctions into the adjacent sequences. In each case there was an open reading frame for at least 200 basepairs upstream of the ura3 gene in frame with the ura3 gene. These sequences were compared to the sequences in GeneBank and one clone turned out to show homology. It contained an in frame fusion to the p1 protein of the TYA open reading frame of the Ty1 transposon see a publication entitled "Variants within the yeast Ty sequence family encode a class of structurally conserved proteins" published by Fulton et al. in Nucleic Acids Research in volume 13 on pages 4097–4112. In frame fusion occurred after nucleotide 1128 or after amino acid 376 of the p1 protein. This again documents that the URA3 protein functions very well even as a fusion protein of more than twice its size. These data prove clearly that the promoterless ura3 gene integrates in frame into expressed genomic genes as used in our process.

We claim:

1. A process for insertional mutagenesis and genome manipulations of yeast cells comprising the steps of:
  (a) transforming viable yeast cells with a restriction enzyme cleaved deoxyribonucleic acid fragment, which lacks substantial sequence identity and shows no specific hybridization signals with the DNA of said viable yeast cells, comprising a selectable marker, so that said cleaved deoxyribonucleic acid fragment is incorporated into said yeast cells by nonhomologous recombination;
  (b) incubating said yeast cells transformed with said cleaved deoxyribonucleic acid fragment in the presence of a growth medium which selects those cells which contain said deoxyribonucleic acid fragment based on said selectable marker, thereby providing incubated yeast cells; and
  (c) identifying which of said incubated yeast cells contain said deoxyribonucleic acid fragment thereby achieving said insertional mutagenesis and genome manipulations.

2. The process as recited in claim 1, wherein said yeast cells are *Saccharomyces cerevisiae* yeast cells, and wherein said yeast cells and said restriction enzyme cleaved deoxyribonucleic acid fragment are combined with a restriction enzyme.

3. A process for insertional mutagenesis and for genome manipulations of mammalian cells, comprising the steps of:
  (a) transforming viable mammalian cells comprised of genomic deoxyribonucleic acid material with a restriction enzyme cleaved deoxyribonucleic acid fragment comprising a selectable marker and a restriction enzyme, so that said cleaved deoxyribonucleic acid fragment is incorporated into said mammalian cells by restriction enzyme mediated recombination;
  (b) incubating said mammalian cells transformed with said cleaved deoxyribonucleic acid fragment in the presence of a growth medium which selects those cells which contain said deoxyribonucleic acid fragment based on said selectable marker, thereby yielding incubated mammalian cells; and
  (c) identifying which of said incubated mammalian cells contain said deoxyribonucleic acid fragment thereby achieving said insertional mutagenesis and genome manipulations.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharomyces cerevisiae
        ( B ) STRAIN: S35/2-10C ( v i i i ) POSITION IN GENOME:
        ( A ) CHROMOSOME/SEGMENT: Chromosome 5

( x i ) SEQUENCE DESCRIPTION: SEQ ID NO:1:

CGGAGATTAC CGAATCAA         18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharomyces cerevisiae
        ( B ) STRAIN: S35/2-10C ( v i i i ) POSITION IN GENOME:
        ( A ) CHROMOSOME/SEGMENT: Chromosome 5

( x i ) SEQUENCE DESCRIPTION: SEQ ID NO:2:

GAATCTCGGT CGTAATGA         18

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Saccharomyces cerevisiae
    ( B ) STRAIN: S35/2-10C ( v i i i ) POSITION IN GENOME:
    ( A ) CHROMOSOME/SEGMENT: Chromosome 5

( x i ) SEQUENCE DESCRIPTION: SEQ ID NO:3:

CGCGAATTCC TTCACCATAA ATATGCCTCG          30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharomyces cerevisiae
        ( B ) STRAIN: S35/2-10C ( v i i i ) POSITION IN GENOME:
        ( A ) CHROMOSOME/SEGMENT: Chromosome 5

( x i ) SEQUENCE DESCRIPTION: SEQ ID NO:4:

ATATCCCGGG AACTATCCAA TACCTCGGCA          30

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharomyces cerevisiae
        ( B ) STRAIN: S35/2-10C ( v i i i ) POSITION IN GENOME:
        ( A ) CHROMOSOME/SEGMENT: Chromosome 5

( x i ) SEQUENCE DESCRIPTION: SEQ ID NO:5:

CGCGGATCCT ATAAGGAACG TGCTGCTACT CAT          33

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (vi) ORIGINAL SOURCE:
  (A) ORGANISM: Saccharomyces cerevisiae
  (B) STRAIN: S35/2-10C (viii) POSITION IN GENOME:
  (A) CHROMOSOME/SEGMENT: Chromosome 5

(xi) SEQUENCE DESCRIPTION: SEQ ID NO:6:

```
CGCGGATCCC GGGTAATAAC TGATATAA                                    28
```